(12) United States Patent
Bedard et al.

(10) Patent No.: US 9,358,137 B2
(45) Date of Patent: Jun. 7, 2016

(54) ACTUATED PROSTHESIS FOR AMPUTEES

(75) Inventors: Stephane Bedard, Quebec (CA); Pierre-Olivier Roy, Quebec (CA)

(73) Assignee: Victhom Laboratory Inc., Laval, QC (CA)

( * ) Notice: Subject to any disclaimer, the term of this patent is extended or adjusted under 35 U.S.C. 154(b) by 0 days.

(21) Appl. No.: 12/815,166

(22) Filed: Jun. 14, 2010

(65) Prior Publication Data
US 2010/0262260 A1 Oct. 14, 2010

Related U.S. Application Data

(63) Continuation of application No. 10/721,764, filed on Nov. 25, 2003, now Pat. No. 7,736,394, which is a continuation-in-part of application No. 10/463,495, filed on Jun. 17, 2003, now Pat. No. 7,314,490.

(60) Provisional application No. 60/405,281, filed on Aug. 22, 2002, provisional application No. 60/424,261, filed on Nov. 6, 2002, provisional application No. 60/453,556, filed on Mar. 11, 2003.

(51) Int. Cl.
*A61F 2/66* (2006.01)
*A61F 2/64* (2006.01)
(Continued)

(52) U.S. Cl.
CPC ... *A61F 2/66* (2013.01); *A61F 2/64* (2013.01); *A61F 2/644* (2013.01); *A61F 2/68* (2013.01); *A61F 2/6607* (2013.01); *A61F 2002/30359* (2013.01); *A61F 2002/5041* (2013.01); *A61F 2002/607* (2013.01); *A61F 2002/6614* (2013.01); *A61F 2002/6685* (2013.01); *A61F 2002/701* (2013.01); *A61F 2002/704* (2013.01); *A61F 2002/705* (2013.01); *A61F 2002/741* (2013.01); *A61F 2002/762* (2013.01); *A61F 2002/764* (2013.01); *A61F 2002/7625* (2013.01); *A61F2002/7635* (2013.01); *A61F 2220/0033* (2013.01)

(58) Field of Classification Search
USPC .................. 623/FOR. 39, FOR. 43, FOR. 44, 623/FOR. 45
See application file for complete search history.

(56) References Cited

U.S. PATENT DOCUMENTS 909,859 A 1/1909 Apgar
2,568,051 A 9/1951 Catranis
(Continued)

FOREIGN PATENT DOCUMENTS

CH 543277 12/1973
CN 2043873 9/1989
(Continued)

OTHER PUBLICATIONS

U.S. Appl. No. 60/395,938, filed Jul. 15, 2002.*
(Continued)

*Primary Examiner* — David H Willse
(74) *Attorney, Agent, or Firm* — Knobbe, Martens, Olson & Bear LLP

(57) ABSTRACT

The actuated leg prosthesis comprises a knee member, a socket connector provided over the knee member, an elongated trans-tibial member having a bottom end under which is connected an artificial foot, and a linear actuator. A first pivot assembly allows to operatively connect the trans-tibial member to the knee member. A second pivot assembly allows to operatively connect an upper end of the actuator to the knee member. A third pivot assembly allows to operatively connect a bottom end of the actuator to the bottom end of the trans-tibial member. The prosthesis can be provided as either a front actuator configuration or a rear actuator configuration.

47 Claims, 17 Drawing Sheets

(51) Int. Cl.
*A61F 2/68* (2006.01)
*A61F 2/30* (2006.01)
*A61F 2/50* (2006.01)
*A61F 2/60* (2006.01)
*A61F 2/70* (2006.01)
*A61F 2/74* (2006.01)
*A61F 2/76* (2006.01)

(56) References Cited

U.S. PATENT DOCUMENTS

| | | |
|---|---|---|
| 2,619,652 A | 12/1952 | Vesper |
| 2,843,853 A | 7/1958 | Mauch |
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,589,134 A | 6/1971 | Hackmann |
| 3,659,294 A | 5/1972 | Glabiszewski |
| 3,701,368 A | 10/1972 | Stern |
| 3,791,375 A | 2/1974 | Pfeifer |
| 3,820,168 A | 6/1974 | Horvath |
| 3,866,246 A | 2/1975 | Seamone et al. |
| 3,871,032 A | 3/1975 | Karas |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Young et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,012,591 A | 5/1991 | Asakawa |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Berringer et al. |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnas |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnas |
| 5,376,137 A | 12/1994 | Shorter et al. |
| 5,376,138 A | 12/1994 | Bouchard et al. |
| 5,376,141 A | 12/1994 | Phillips |
| 5,382,373 A | 1/1995 | Carlson et al. |
| 5,383,939 A | 1/1995 | James |
| 5,394,132 A | 2/1995 | Poil |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,472,412 A | 12/1995 | Knoth |
| 5,476,441 A | 12/1995 | Durfee et al. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford et al. |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |

(56) References Cited

U.S. PATENT DOCUMENTS

| | | |
|---|---|---|
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriguez |
| 5,800,568 A | 9/1998 | Atkinson et al. |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | Van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,947,238 A | 9/1999 | Jolly et al. |
| 5,948,021 A | 9/1999 | Radcliffe |
| 5,955,667 A | 9/1999 | Fyfe |
| 5,957,981 A | 9/1999 | Grammas |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,998,930 A | 12/1999 | Upadhyay et al. |
| 6,006,412 A | 12/1999 | Bergmann et al. |
| 6,007,582 A | 12/1999 | May |
| RE36,521 E | 1/2000 | Hiemisch |
| 6,039,091 A | 3/2000 | Rodgers et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,690 A | 10/2000 | Hamlin et al. |
| 6,139,586 A | 10/2000 | Wagner et al. |
| 6,165,226 A | 12/2000 | Wagner |
| 6,168,634 B1 | 1/2001 | Schmitz |
| 6,183,425 B1 | 2/2001 | Whalen et al. |
| 6,187,051 B1 | 2/2001 | van de Veen |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,241,775 B1 | 6/2001 | Blatchford |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,379,393 B1 | 4/2002 | Mavroidis et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundel |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,537,322 B1 | 3/2003 | Johnson et al. |
| 6,587,728 B2 | 7/2003 | Fang et al. |
| 6,589,287 B2 | 7/2003 | Lundborg |
| 6,599,439 B2 | 7/2003 | Iregar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,645,252 B2 | 11/2003 | Asai et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,719,806 B1 | 4/2004 | Zahedi et al. |
| 6,733,180 B2 | 5/2004 | Nakamura |
| 6,740,123 B2 | 5/2004 | Davalli et al. |
| 6,740,125 B2 | 5/2004 | Mosler |
| 6,743,260 B2 | 6/2004 | Townsend et al. |
| 6,755,870 B1 | 6/2004 | Biedermann et al. |
| 6,761,743 B1 | 7/2004 | Johnson |
| 6,764,520 B2 | 7/2004 | Herr et al. |
| 6,770,045 B2 | 8/2004 | Naft et al. |
| 6,780,343 B2 | 8/2004 | Hata et al. |
| 6,805,677 B2 | 10/2004 | Simmons |
| 6,811,571 B1 | 11/2004 | Phillips |
| 6,813,582 B2 | 11/2004 | Levi et al. |
| D499,487 S | 12/2004 | Bedard et al. |
| D501,925 S | 2/2005 | Bedard et al. |
| 6,855,170 B2 | 2/2005 | Gramnas |
| 6,875,241 B2 | 4/2005 | Christensen |
| 6,876,135 B2 | 4/2005 | Pelrine et al. |
| 6,908,488 B2 | 6/2005 | Passivaara |
| 6,910,331 B2 | 6/2005 | Asai et al. |
| 6,918,308 B2 | 7/2005 | Biedermann |
| 6,966,882 B2 | 11/2005 | Horst |
| 6,966,933 B2 | 11/2005 | Christensen |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,066,896 B1 | 6/2006 | Kiselik |
| 7,066,964 B2 | 6/2006 | Wild |
| 7,101,487 B2 | 9/2006 | Hsu et al. |
| 7,118,601 B2 | 10/2006 | Yasui |
| 7,131,998 B2 | 11/2006 | Pasolini |
| 7,137,998 B2 | 11/2006 | Bedard et al. |
| 7,147,667 B2 | 12/2006 | Bedard |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,198,071 B2 | 4/2007 | Bisbee, III et al. |
| 7,209,788 B2 | 4/2007 | Nicolelis et al. |
| 7,279,009 B2 | 10/2007 | Herr et al. |
| 7,295,892 B2 | 11/2007 | Herr et al. |
| 7,314,490 B2 | 1/2008 | Bedard et al. |
| 7,381,192 B2 | 6/2008 | Brodard |
| 7,396,337 B2 | 7/2008 | McBean et al. |
| 7,410,338 B2 | 8/2008 | Schiele et al. |
| 7,410,471 B1 | 8/2008 | Campbell et al. |
| 7,410,472 B2 | 8/2008 | Yakimovich et al. |

(56) References Cited

U.S. PATENT DOCUMENTS

| | | | |
|---|---|---|---|
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,485,152 B2 | 2/2009 | Haynes et al. |
| 7,503,900 B2 | 3/2009 | Goswami |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,588,604 B2 | 9/2009 | Okuda |
| 7,637,957 B2 | 12/2009 | Ragnarsdóttir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bedard et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bedard et al. |
| 7,867,284 B2 | 1/2011 | Bedard |
| 7,896,927 B2 | 3/2011 | Clausen et al. |
| 7,918,808 B2 | 4/2011 | Simmons |
| 7,942,935 B2 | 5/2011 | Iversen et al. |
| 7,955,398 B2 | 6/2011 | Bedard et al. |
| 8,007,544 B2 | 8/2011 | Jonsson et al. |
| 8,048,007 B2 | 11/2011 | Roy |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,109,890 B2 | 2/2012 | Kamiar et al. |
| 8,231,687 B2 | 7/2012 | Bedard et al. |
| 8,287,477 B1 | 10/2012 | Herr et al. |
| 8,323,354 B2 | 12/2012 | Bedard et al. |
| 8,403,997 B2 | 3/2013 | Sykes et al. |
| 8,435,309 B2 | 5/2013 | Gilbert et al. |
| 8,657,886 B2 | 2/2014 | Clausen et al. |
| 8,702,811 B2 | 4/2014 | Ragnarsdottir et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 2001/0029400 A1 | 10/2001 | Deffenbaugh et al. |
| 2002/0052663 A1 | 5/2002 | Herr et al. |
| 2002/0087216 A1 | 7/2002 | Atkinson et al. |
| 2002/0198604 A1 | 12/2002 | Schulman et al. |
| 2003/0019700 A1 | 1/2003 | Wittig |
| 2003/0120183 A1* | 6/2003 | Simmons ............ 600/595 |
| 2004/0064195 A1 | 4/2004 | Herr |
| 2004/0083007 A1 | 4/2004 | Molino et al. |
| 2004/0193286 A1 | 9/2004 | Grundel |
| 2005/0107889 A1 | 5/2005 | Bedard et al. |
| 2005/0283257 A1 | 12/2005 | Bisbee et al. |
| 2006/0069336 A1 | 3/2006 | Krebs et al. |
| 2006/0184280 A1 | 8/2006 | Oddsson et al. |
| 2006/0201757 A1 | 9/2006 | Dupuis et al. |
| 2006/0249315 A1 | 11/2006 | Herr et al. |
| 2006/0259153 A1 | 11/2006 | Harn et al. |
| 2007/0016329 A1 | 1/2007 | Herr et al. |
| 2007/0027557 A1 | 2/2007 | Jonsson et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2008/0004718 A1 | 1/2008 | Mosler |
| 2008/0046096 A1 | 2/2008 | Bedard et al. |
| 2008/0097269 A1 | 4/2008 | Weinberg et al. |
| 2008/0306612 A1 | 12/2008 | Mosler |
| 2010/0113980 A1 | 5/2010 | Herr et al. |
| 2010/0131101 A1 | 5/2010 | Engeberg et al. |
| 2010/0262260 A1 | 10/2010 | Bedard et al. |
| 2010/0324456 A1 | 12/2010 | Jónsson et al. |
| 2010/0324699 A1 | 12/2010 | Herr et al. |
| 2011/0106274 A1 | 5/2011 | Ragnarsdottir et al. |
| 2011/0125290 A1 | 5/2011 | Langlois |
| 2011/0130847 A1 | 6/2011 | Bedard et al. |
| 2011/0137429 A1 | 6/2011 | Bedard |
| 2011/0224804 A1 | 9/2011 | Clausen et al. |
| 2012/0016492 A1 | 1/2012 | Clausen |
| 2012/0191221 A1 | 7/2012 | Bedard et al. |
| 2012/0209405 A1 | 8/2012 | Herr et al. |
| 2012/0232672 A1 | 9/2012 | Ragnarsdottir et al. |
| 2012/0283844 A1 | 11/2012 | Langlois |
| 2013/0035769 A1 | 2/2013 | Bedard et al. |
| 2013/0144402 A1 | 6/2013 | Clausen et al. |
| 2013/0204395 A1 | 8/2013 | Gramnaes |
| 2013/0268093 A1 | 10/2013 | Gilbert et al. |
| 2013/0297041 A1 | 11/2013 | Bedard et al. |
| 2014/0243997 A1 | 8/2014 | Clausen et al. |

FOREIGN PATENT DOCUMENTS

| | | | |
|---|---|---|---|
| CN | 1215614 | | 5/1999 |
| CN | 2400072 Y | | 10/2000 |
| DE | 3543291 | | 6/1987 |
| DE | 3923056 | | 1/1991 |
| DE | 3923057 | | 1/1991 |
| DE | 42 29 330 A1 | | 3/1994 |
| DE | 19859931 A1 | | 7/2007 |
| EP | 0358056 | | 3/1990 |
| EP | 0380060 | | 8/1990 |
| EP | 0 549 855 A2 | | 7/1993 |
| EP | 0549855 | | 7/1993 |
| EP | 0654254 | | 5/1995 |
| EP | 0902547 | | 3/1999 |
| EP | 1125825 | | 1/2001 |
| EP | 1107420 | | 6/2001 |
| EP | 1 166 726 A1 | | 1/2002 |
| EP | 1 169 982 A1 | | 1/2002 |
| EP | 1 410 780 | | 4/2004 |
| EP | 1 442 704 | | 8/2004 |
| EP | 1 547 567 | | 6/2005 |
| FR | 2 293 185 | | 7/1976 |
| FR | 2 623 086 | | 5/1989 |
| FR | 2 816 463 | | 5/2002 |
| GB | 2 201 260 | | 8/1988 |
| GB | 2244006 | | 11/1991 |
| GB | 2 260 495 | | 4/1993 |
| GB | 2301776 | | 12/1996 |
| GB | 2 302 949 A | | 2/1997 |
| GB | 2338653 | | 12/1999 |
| GB | 2343848 | | 5/2000 |
| GB | 2367753 | | 4/2002 |
| JP | 59-32453 | | 2/1984 |
| JP | 60-081530 | | 5/1985 |
| JP | 60-177102 | | 9/1985 |
| JP | 59-189843 | | 10/1985 |
| JP | 01-244748 | | 9/1989 |
| JP | 03-181633 | | 8/1991 |
| JP | 04-78337 | | 3/1992 |
| JP | 05-123348 | | 5/1993 |
| JP | 5-161668 | | 6/1993 |
| JP | 7-24766 | | 1/1995 |
| JP | 11-000345 | | 1/1999 |
| JP | 11-056885 | | 3/1999 |
| JP | 11056885 | | 3/1999 |
| JP | 11-215793 A * | 8/1999 | ............... A61F 2/72 |
| JP | 2001-277175 | | 10/2001 |
| JP | 2001277175 | | 10/2001 |
| JP | 2002-191654 A | | 7/2002 |
| JP | 2002-219141 | | 8/2002 |
| JP | 2002/533161 | | 10/2002 |
| JP | 2005-500 | | 1/2005 |
| KR | 2002/0041137 | | 6/2002 |
| SU | 1447366 | | 12/1988 |
| SU | 1731210 | | 5/1992 |
| WO | WO 94/06374 | | 3/1994 |
| WO | WO 94/09727 | | 5/1994 |
| WO | WO 95/26171 | | 10/1995 |
| WO | WO 96/39110 | | 12/1996 |
| WO | WO 96/41599 | | 12/1996 |
| WO | WO 97/00661 | | 1/1997 |
| WO | WO 97/27822 A * | 8/1997 | ............... A61F 2/68 |
| WO | WO 98/38951 | | 9/1998 |
| WO | WO 99/00075 | | 1/1999 |

(56) References Cited

FOREIGN PATENT DOCUMENTS

| WO | WO 99/05991 | 2/1999 |
|---|---|---|
| WO | WO 99/08621 | 2/1999 |
| WO | WO 99/55261 | 11/1999 |
| WO | WO 00/27318 | 5/2000 |
| WO | WO 00/30572 | 6/2000 |
| WO | WO 00/38599 | 7/2000 |
| WO | WO 01/17466 | 3/2001 |
| WO | WO01/54630 | 8/2001 |
| WO | WO 01/72245 | 10/2001 |
| WO | WO 02/080825 | 10/2002 |
| WO | WO 03/003953 | 1/2003 |
| WO | WO 03/088373 | 10/2003 |
| WO | WO 2004/017890 | 3/2004 |
| WO | WO 2005/051248 | 6/2005 |
| WO | WO2005/087144 | 9/2005 |

OTHER PUBLICATIONS

Australian Search Report, Nov. 25, 2005.
European Office Action dated Aug. 17, 2009 in Application No. 04 802 212.3, filed Nov. 25, 2004.
Indian Office Action dated Oct. 13, 2008 in Application No. 1424/KOLNP/2006, filed May 26, 2006.
International Preliminary Report and Written Opinion, PCT/CA2004/002035, filed Nov. 25, 2004, date of issuance May 29, 2006.
Dietl, H., Der Einsatz von Elektronik bei Prothesen zur Versorgung der unteren Extremitat, Med. Orth. Tech. 117 (1997) 31-35.
English translation of EP 1 169 982 A1.
English translation of Ota, JP 2002-191654 A.
EPO—International Search Report, Dec. 5, 2003, PCT/CA03/00902.
Flowers et al., Journal of Biomechanical Engineering: Transactions of the ASME: Feb. 1977, pp. 3-8.
Japanese Office Action dated Apr. 6, 2010, Patent Application No. 2006-540123, 5 pages.
Canadian Office Action dated Apr. 9, 2010 in Application No. 2,546,858.
Chinese Office Action dated Jun. 24, 2010 in Application No. 20040039143.8, filed Nov. 25, 2004.
Blaya, Force-Controllable Ankle Foot Orthosis (AFO) to Assist Drop Foot Gait, Feb. 2003 (believed to be catalogued on or after Jul. 8, 2003).
Flowers et al., "An Electrohydraulic Knee-Torque Controller . . . "; J. Biomed. Eng., Transaction of the ASME; Feb. 1977; pp. 3-8.
Hanafusa et al., "A Robot Hand with Elastic Fingers and Its Application to Assembly Process," pp. 337-359, Robot Motion, Brady et al., MIT Press, Cambridge, MA, 1982.
Howard, "Joint and Actuator Design for Enhanced Stability in Robotic Force Control," Ph.D. thesis, Massachusetts Inst. of Technology, Dept. of Aeronautics and Astronautics, 1990.
Pfeffer et al. , "Experiments with a Dual-Armed, Cooperative, Flexible-Drivetrain Robot System," Proc. 1993 IEEE Int. Conf. on Robotics & Automation, vol. 3, pp. 601-608, May 5, 1993.
Rapport De Recherche Europeenne EP 01169982, mailed on Nov. 6, 2001.
Sugano et al., "Force Control of the Robot Finger Joint equipped with Mechanical Compliance Adjuster," Proc. 1992 IEEE/RSJ Int. Conf. on Intell. Robots & Sys., pp. 2005-2013, Jul. 1992.
Murray, Ph.D., M.P., et al., Walking Patterns of Normal Men, The Journal of Bone and Joint Surgery 46-A(2):335-360, Mar. 1964.
Abbas, J.J., et al., Neural Network Control of Functional Neuromuscular Stimulation Systems: Computer Stimulation Studies, IEEE Transactions on Biomedical Engineering 42(11), Nov. 1995.
Aminian, K., et al., Estimation of Speed and Incline of Walking Using Neural Network, IEEE Transactions on Instrumentation and Measurement 44(3):743-746, Jun. 1995.
Andrews, B.J., et al., Hybrid FES Orthosis Incorporating Closed Loop Control and Sensory Feedback, J. Biomed. Eng. 10:189-195, Apr. 1988.

Bachmann, E., et al., Inertial and Magnetic Tracking of Limb Segment Orientation for Inserting Humans into Synthetic Environments, Naval Postgraduate School Dissertation, Dec. 2000.
Bar, A., et al., Adaptive Microcomputer Control of an Artificial Knee in Level Walking, J. Biomechanical Eng. 5:145-150, Apr. 1983.
Baten, C., et al., Inertial Sensing in Ambulatory Back Load Estimation, $18^{th}$ Annual International Conference of the IEEE Engineering in Medicine and Biology Society, Amsterdam, 1996, pp. 497-498.
Blumentritt, Ph.D., S., et al. Design Principles, Biomedical Data and Clinical Experience with a Polycentric Knee Offering Controlled Stance Phase Knee Flexion: A Preliminary Report, Journal of Prosthetics and Orthotics 9(1)18-24, 1997.
Bogert, A., et al., A Method for Inverse Dynamic Analysis Using Accelerometry, J. Biomechanics 29(7):949-954, 1996.
Bortz, J., A New Mathematical Formulation for Strapdown Inertial Navigation, IEEE Transactions on Aerospace and Electronic Systems AES-7(1), Jan. 1971.
Bouten, C.V., et al., A Triaxial Accelerometer and Portable Data Processing Unit for the Assessment of Daily Physical Activity, IEEE Transactions on Biomedical Engineering 44(3):136-147, Mar. 1997.
Bouten, C.V., et al., Assessment of Energy Expenditure for Physical Activity Using a Triaxial Accelerometer, Medicine and Science in Sports and Exercise 26(12), Aug. 1994, 1516-1523.
Carlson, J.D., et al., Smart Prosthetics Based on Magnetorheological Fluids, Proceedings of the 8th Annual Symposium on Smart Structures and Materials, Newport Beach, CA, Mar. 2001.
C-Leg System, Otto Bock, available at http://web.archive.org/web/20040215152410/http:/www.ottobockus.com/products/lower_limb_prosthetics/c-leg.asp, retrieved Mar. 8, 2013.
Copes/Bionic Ankle, Copes, Inc., copyright 1985.
Crago, P.E., et al., New Control Strategies for Neuroprosthetic Systems, Journal of Rehabilitation Research and Development 33(2), Apr. 1996, 158-172.
Dai, R., et al., Application of Tilt Sensors in Functional Electrical Stimulation, IEEE Transactions on Rehabilitation Engineering 4(2):63-71, Jun. 1996.
European Search Report in European Application No. 12178503.4, Nov. 20, 2012.
Fisekovic, N. et al., New Controller for Functional Electrical Stimulation Systems, Medical Engineering & Physics 23:391-399, 2000.
Foerster, F., et al., Detection of Posture and Motion by Accelerometry: A Validation Study in Ambulatory Monitoring, Computers in Human Behavior 15:571-583, 1999.
Foxlin, E., et al., Miniature 6-DOF Inertial System for Tracking HMDs, SPIE 3362, Helmet and Head-Mounted Displays III, AeroSense 98, Orlando, FL, Apr. 13-14, 1998.
Frank, K., et al., Reliable Real-Time Recognition of Motion Related Human Activities Using MEMS Inertial Sensors, 2010.
Fujita, K., et al., Joint Angle Control with Command Filter for Human Ankle Movement Using Functional Electrical Stimulation, Proceedings of the 9th Annual Conference of the IEEE Engineering in Medicine and Biology Society, Boston, MA, Nov. 13-16, 1987.
Gelat, T., et al., Adaptation of the Gait Initiation Process for Stepping on to a New Level Using a Single Step, Exp. Brain Res. 133:538-546, 2000.
Graps, A., An Introduction to Wavelets, IEEE Computational Science & Engineering, pp. 50-61, Summer 1995.
Grimes, D., An Active Multi-Mode Above-Knee Prosthesis Controller, Doctoral Thesis, Massachusetts Institute of Technology, Jun. 1979, 158 pages.
Gronqvist, R., et al., Human-Centered Approaches in Slipperiness Measurement, Ergonomics 44(13):1167-1199, Oct. 20, 2001.
Hanson, J.P., et al., Predicting Slips and Falls Considering Required and Available Friction, Ergonomics 42(12):1619-1633, 1999.
Hayes, W.C., et al., Leg Motion Analysis During Gait by Multiaxial Accelerometry: Theoretical Foundations and Preliminary Validations, Journal of Biomechanical Engineering 105:283-289, Aug. 1983.
Herr, H., et al., Patient-Adaptive Prosthetic and Orthotic Leg Systems, Proceedings of the 12th Nordic Baltic Conference on Biomedical Engineering and Medical Physics and Proceedings of the International Federation for Medical & Biological Engineering, 2002.

(56) References Cited

OTHER PUBLICATIONS

Herr, H., et al., User-Adaptive Control of a Magnetorheological Prosthetic Knee, Industrial Robot: An International Journal 30(1):42-55, 2003.

Herr, H., Presentation at Experiencing the Frontiers of Biomedical Technology, Harvard Medical School, Boston, MA, Mar. 10-11, 2003, 1 page.

Heyn, A., et al., The Kinematics of the Swing Phase Obtained From Accelerometer and Gyroscope Measurements, 18th Annual International Conference of the IEEE Engineering in Medicine and Biology Society, Amsterdam, 1996, pp. 463-464.

Hill, S.W., et al., Altered Kinetic Strategy for the Control of Swing Limb Elevation Over Obstacles in Unilateral Below-Knee Amputee Gait, Journal of Biomechanics 32:545-549, 1999.

Jonic, S., et al., Three Machine Learning Techniques for Automatic Determination of Rules to Control Locomotion, IEEE Transactions on Biomedical Engineering 46(3):300-310, Mar. 1999.

Kidder, S.M., et al., A System for the Analysis of Foot and Ankle Kinematics During Gait. IEEE Transactions on Rehabilitation Engineering 4(1):25-32, Mar. 1996.

Kirkwood, C.A., et al., Automatic Detection of Gait Events: A Case Study Using Inductive Learning Techniques J. Biomed. Eng. 11:511-516, 1989.

Kirsner, S., A Step in the Right Direction Biomedical Horizons Expanding, Boston Globe, Mar. 17, 2003.

Kostov, A., et al., Machine Learning in Control of Functional Electrical Stimulation Systems for Locomotion, IEEE Transactions on Biomedical Engineering 42(6):543-551, Jun. 1995.

Kuster, M.D., M., et al., Kinematic and Kinetic Comparison of Downhill and Level Walking, Clinical Biomechanics 10(2):79-84, 1995.

Lafortune, M.A., Three Dimensional Acceleration of the Tibia During Walking and Running, J. Biomechanics 24(10)877-886, 1991.

Lee, S., and K. Mase, Activity and Location Recognition Using Wearable Sensors, Pervasive Computing, IEEE, 2002, pp. 24-32.

Light, L.H., et al., Skeletal Transients on Heel Strike in Normal Walking with Different Footwear, J. Biomechanics 13:477-480, 1980.

Luinge, H.J., Inertial Sensing of Movement, Doctoral Thesis, Twente University Press, Enschede, The Netherlands, 2002, pp. 9-13. (88 pages).

Magnetic Fluid Improves Mobility of Prosthetic Leg, Advanced Materials & Processes 9(161): 29-30, Sep. 2003.

Martin, J.J., Electronically Controlled Magnetorheological Fluid Prosthetic Foot, U.S. Appl. No. 60/371,974, filed Apr. 12, 2002.

Mayagoitia, R.E., et al., Accelerometer and Rate Gyroscope Measurement of Kinematics: An Inexpensive Alternative to Optical Motion Analysis Systems, Journal of Biomechanics 35:537-542, 2002.

Moe-Nilssen, R., A New Method for Evaluating Motor Control in Gait Under Real-Life Environmental Conditions, Part 1: The Instrument, Clinical Biomechanics 13:320-327, 1998.

Moe-Nilssen, R., A New Method for Evaluating Motor Control in Gait Under Real-Life Environmental Conditions, Part 2: Gait Analysis, Clinical Biomechanics 13:328-335, 1998.

Morris, J.R.W., Accelerometry—A Technique for the Measurement of Human Body Movements, J. Biomechanics 6:729-736, 1973.

Moseley, A.M., et al., High- and Low-Ankle Flexibility and Motor Task Performance, Gait and Posture 18:73-80, 2003.

Nadeau, S., et al., Frontal and Sagittal Plane Analyses of the Stair Climbing Task in Healthy Adults Aged Over 40 Years: What Are the Challenges Compared to Level Walking? Clinical Biomechanics 18:950-959, 2003.

Nakagawa, A., Intelligent Knee Mechanism and the Possibility to Apply the Principle to the Other Joints, Proceedings of the 20th Annual International Conference of the IEEE Engineering in Medicine and Biology Society 20(5):2282-2287, Dec. 1998.

C-Leg Fitting Statistics, Abstract, Otto Bock Orthopadische Industrie GmbH & Co., Mar. 2000, 4 pages.

C-Leg: A New Dimension in Amputee Mobility, Otto Bock Data Sheet, Otto Bock Orthopadische Industrie, copyright 1997, 4 pages.

The Electronic C-Leg Compact Leg Prosthesis System, Instructions for Use, Otto Bock Orthopadische Industrie, copyright 2002, 28 pages.

The Electronic C-Leg Knee Joint System, Instructions for Use, Otto Bock Orthopadische Industrie, copyright 2002, available at http://www.ottobockus.com/products/lower_limb_prosthetics/c-leg_instructions.pdg, retrieved Jul. 20, 2006, 32 pages.

Otto, J., Prosthetic Knees: What's Currently New and Impressive? The O&P Edge, available at http://www.oandp.com/edge/issues/articles/2003-10_03.asp, 4 pages (printed Oct. 2003).

Otto, J. Prosthetic Knees: What's on the Way? The O&P edge, http://www.oandp.com/edge/issues/articles/2003-10_02.asp, Oct. 2003, 5 pages.

Petrofsky, J.S., et al., Feedback Control System for Walking in Man, Comput. Biol. Med. 14(2):135-149, 1984.

Popovic, D., et al., Control Aspects of Active Above-Knee Prosthesis, International Journal of Man-Machine Machine Studies 35(6)751-767, Dec. 1991.

Powers, C.M., Ph.D., et al., Stair Ambulation in Persons With Transtibial Amputation: An Analysis of the Seattle LightFoot, Journal of Rehabilitation Research and Development 34(1):9-18, Jan. 1997.

Rao, S.S., et al., Segment Velocities in Normal and Transtibial Amputees: Prosthetic Design Implications, IEEE Transactions on Rehabilitation Engineering 6(2):219-226, Jun. 1998.

Redfern, M.S., et al., Biomechanics of Descending Ramps, Gait and Posture 6:119-125, 1997.

Reiner, R., et al., Stair Ascent and Descent at Different Inclinations, Gait and Posture 15:32-44, 2002.

Reitman, J.S., et al., Gait Analysis in Prosthetics: Opinions, Ideas, and Conclusions, Prosthetics and Orthotics International 26:50-57, 2002.

Robinson, D.W., Design and Analysis of Series Elasticity in Closed-Loop Actuator Force Control, MIT Department of Mechanical Engineering, Jun. 1996.

Robinson, D.W., et al., Series Elastic Actuator Development for a Biomimetic Walking Robot, MIT Leg Laboratory, 1999.

Schmalz, T., et al., Energy Efficiency of Trans-Femoral Amputees Walking on Computer-Controlled Prosthetic Knee Joint "C-Leg," Proceedings of the International Society for Prosthetics and Orthotics, 1998.

Sekine, M. et al., Classification of Waist-Acceleration Signals in a Continuous Walking Record, Medical Engineering & Physics 22:285-291, 2000.

Sin, S.W., et al., Significance of Non-Level Walking on Transtibial Prosthesis Fitting with Particular Reference to the Effects of Anterior-Posterior Alignment, Journal of Rehabilitation Research and Development 38(1)1-6, Jan./Feb. 2001.

Smidt, G.L., et al., An Automated Accelerometry System for Gait Analysis, J. Biomechanics 10:367-375, 1977.

State-of-the-Art Prosthetic Leg Incorporates Magneto-Rheological Technology, Medical Product Manufacturing News, Nov. 2000, p. 42.

Suga, T., et al., Newly Designed Computer Controlled Knee-Ankle-Foot Orthosis (Intelligent Orthosis), Prosthetics and Orthotics International 22:230-239, 1998.

Thakkar, S., Energy Economy Gait Analysis of an Autoadaptive Prosthetic Knee, Master's Thesis, Massachusetts Institute of Technology, copyright 2002, 58 pages.

Tomovic, R., et al., A Finite State Approach to the Synthesis of Bioengineering Control Systems, IEEE Transactions on Human Factors in Electronics HFE-7(2):65-69, Jun. 1966.

Tong, K.Y., and M.H. Granat, A Practical Gait Analysis System Using Gyroscopes, Medical Engineering & Physics 21(2):87-94, Mar. 1999.

Tong, K.Y., and M.H. Granat, Virtual Artificial Sensor Technique for Functional Electrical Stimulation, Medical Engineering & Physics 20:458-468, 1998.

Townsend, M.A., et al., Biomechanics and Modeling of Bipedal Climbing and Descending, Journal of Biomechanics 9(4):227-239, 1976.

(56) References Cited

OTHER PUBLICATIONS

Van Der Kooij, H., et al., A Multisensory Integration Model of Human Stance Control, Biol. Cybern. 80:299-308, 1999.

Van Der Loos, H.F.M., et al., ProVAR Assistive Robot System Architecture, Proceedings of the IEEE International Conference on Robotics & Automation, Detroit, MI, May 1999, pp. 741-746.

Veltink, P.H., et al., Detection of Static and Dynamic Activities Using Uniaxial Accelerometers, IEEE Transactions on Rehabilitation Engineering 4(4):375-385, 1996.

Veltink, P.H., et al., The Feasibility of Posture and Movement Detection by Accelerometry, in 15th Annual International Conference of the IEEE Engineering in Medicine and Biology Society, Oct. 28-31, 1993, San Diego, CA, pp. 1230-1231.

Wilkenfeld, Ph.D., A., An Auto-Adaptive External Knee Prosthesis, Artificial Intelligence Laboratory, Massachusetts Institute of Technology, Cambridge, MA, Sep. 2000, 3 pages.

Wilkenfeld, Ph.D., A., Biologically Inspired Autoadaptive Control of a Knee Prosthesis, Dissertation Abstract, Massachusetts Institute of Technology, Cambridge, Massachusetts, Sep. 2000, 1 page.

Willemsen, A.Th.M., et al., Automatic Stance-Swing Phase Detection from Accelerometer Data for Peroneal Nerve Stimulation, IEEE Transactions on Biomedical Engineering 37(12):1201-1208, Dec. 1990.

Willemsen, A.Th.M., et al., Real-Time Gait Assessment Utilizing a New Way of Accelerometry. J. Biomechanics 23(8):859-863, 1990.

Williamson, M.M., Series Elastic Actuators, Massachusetts Institute of Technology Artificial Intelligence Laboratory, A.I. Technical Report No. 1524, Jan. 1995, pp. 1-83.

Woodward, M.I., et al., Skeletal Accelerations Measured During Different Exercises, Proceedings of the Institution of Mechanical Engineers, Part H: Journal of Engineering Medicine, 207:79-85, 1993.

Wu, G., The Study of Kinematic Transients in Locomotion Using the Integrated Kinematic Sensor, IEEE Transactions on Rehabilitation Engineering 4(3):193-200, Sep. 1996.

Carlson, J. David, What makes a Good MR Fluid?, 8th International Conference on Electrorheological (ER) Fluids and magnetorheological (MR) Suspensions, Nice 7 pages, Jul. 9-13, 2001.

Flowers, W.C., A Man-Interactive Simulator System for Above-Knee Prosthetics Studies, Aug. 1972.

Perry, Jacquelin, MD, Gait Analysis: Normal and Pathological Function, 1992.

Sowell, T.T., A Preliminary Clinical Evaluation of the Mauch Hydraulic Foot-Ankle System, 5 Prosthetics and Orthotics International 87 (1981).

Lelas, et al., Hydraulic versus Magnetorheological-based Electronic Knee Protheses: A Clinical Comparison, Harvard Medical School, Dept. of Phys. Med. And Rehab., Boston, MA, 2004, pp. 1-16.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12.

Popovik, D. et al.; Optimal control for an Above-Knee Prosthesis With Two Degrees of Freedom, 1995, pp. 89-98, Jo. Biomechanics, vol. 28, No. 1.

Proteor, Assembly and Adjustment Instructions for IP50-R, pp. 1-21, Sep. 2004.

Hashimoto et al., "An instrumented compliant wrist using a parallel mechanism," Japan/USA Symposium on Flexible Automation, vol. 1, pp. 741-744, ASME, 1992.

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

Sigurdsson et al., $12^{th}$ Nordic Baltic Conference on Biomedical Engineering and Medical Physics : 12 NBC 2002; Jun. 18-22, 2002, Reykjavik, Iceland; regional meeting of IFMBE.

\* cited by examiner

ACTUATED PROSTHESIS FOR AMPUTEES

RELATED APPLICATIONS

The present application is a continuation of U.S. patent application Ser. No. 10/721,764, filed Nov. 25, 2003, issued as U.S. Pat. No. 7,736,394 on Jun. 15, 2010, which is a continuation-in-part of U.S. patent application Ser. No. 10/463,495, filed Jun. 17, 2003, now U.S. Pat. No. 7,314,490, which claims the benefit of priority of U.S. Provisional Patent Application No. 60/405,281, filed Aug. 22, 2002, U.S. Provisional Patent Application No. 60/424,261, filed Nov. 6, 2002, and U.S. Provisional Patent Application No. 60/453,556, filed Mar. 11, 2003, each of which is hereby incorporated by reference in its entirety.

BACKGROUND

1. Field

The present invention relates to an actuated prosthesis for amputees, particularly but not exclusively for a leg prosthesis for above knee amputees.

2. Description of Related Art

Over the years, many kinds of prostheses have been devised in effort to replace the limbs that amputees have lost. In particular, many efforts have been made to develop prostheses that will replace the loss of major limbs such as legs and arms in view of the immense impact that such a loss has on the amputee. All these prostheses have the difficult task of giving to these amputees a life as normal as possible. The task is particularly difficult for leg prostheses due in part to the complexity of human locomotion. Conventional leg prostheses have until now only been using passive mechanisms in the most sophisticated available devices. Conventional leg prostheses are very limited compared to a real human leg and some needs were thus not entirely fulfilled by them.

According to amputees, specific conditions of use of conventional leg prostheses, such as repetitive movements and continuous loading, typically entail problems such as increases in metabolic energy expenditures, increases of socket pressure, limitations of locomotion speeds, discrepancies in the locomotion movements, disruptions of postural balance, disruptions of the pelvis-spinal column alignment, and increases in the use of postural clinical rehabilitation programs.

Another problem is that during the amputees' locomotion, energy used for moving the prosthesis mainly originates from the amputees themselves because conventional leg prostheses do not have self-propulsion capabilities. This has considerable short and long-term negative side effects. Recent developments in the field of energy-saving prosthetic components have partially contributed to improve energy transfer between the amputees and their prosthesis. Nevertheless, the problem of energy expenditure is still not fully resolved and remains a major concern.

A further problem is that the dynamic role played by the stump during the amputees' locomotion renders difficult the prolonged wearing of conventional leg prostheses. This may create, among other things, skin problems such as folliculitis, contact dermatitis, oedema, cysts, skin shearing, scarring and ulcers. Although these skin problems may be partially alleviated by using a silicone sheath, a complete suction socket or powder, minimizing these skin problems remain a concern.

Similar considerations apply in other prostheses, to a greater or lesser extent as dictated by the particular conditions that are imposed on the prosthesis.

It is therefore an object of the present invention to obviate or mitigate the above disadvantages.

SUMMARY

In accordance with a first broad aspect of the present invention, there is provided an actuated prosthesis for replacement of an amputated limb, the prosthesis comprising: a primary joint member; a socket connector assembly for connecting a socket to said primary joint member; an elongated structural member having opposite ends spaced apart along, a main longitudinal axis; a connector assembly for connecting a terminal portion to an end of said structural member; a pivot assembly for operatively connecting the structural member to the primary joint member to permit relative rotation between said primary joint member and said structural member about an first axis defined by said pivot assembly; a linear actuator connected at one end to said structural member and at the opposite end to said primary joint member at a location spaced from said pivot assembly, whereby extension or retraction of said actuator induces a corresponding rotation of said primary joint member relative to said structural member about said pivotal axis.

Preferably, said prosthesis is a leg prosthesis and said actuator is electrically powered.

In accordance with another broad aspect of the present invention, there is provided an improved actuated leg prosthesis comprising a knee member, a socket connected to the knee member, an elongated trans-tibial member, an artificial foot connected under a bottom end of the trans-tibial member, and a linear actuator. A first pivot assembly allows to operatively connect the trans-tibial member to the knee member. The first pivot assembly defines a first pivot axis that is perpendicular to a main longitudinal axis of the trans-tibial member. A second pivot assembly allows to operatively connect an upper end of the actuator to the knee member. The second pivot assembly defines a second pivot axis that is substantially parallel to the first pivot axis. The second pivot axis is also spaced apart from the first pivot axis and the main longitudinal axis. A third pivot assembly allows to operatively connect a bottom end of the actuator to the bottom end of the trans-tibial member. The third pivot assembly defines a third pivot axis that is substantially parallel to and spaced apart from the first pivot axis.

Embodiments of the present invention will now be described by way of example only with reference to the accompanying drawings.

DETAILED DESCRIPTION

The appended figures show three alternative embodiments of an actuated prosthesis (10) implemented as a leg prosthesis for an above knee amputee. It should be understood that the present invention is not limited to these illustrated implementations since various changes and modifications may be effected herein without departing from the scope of the appended claims and the principles and concepts described may be applied to prosthesis to replicate other limbs such as an arm. For clarity and ease of description, terminology relating to the use as a leg has been utilized but it will be understood that terminology applicable to the equivalent functions in other limbs may be used. For example, reference to a "knee" could be described equally with respect to an "elbow" if the prosthesis is an arm.

As illustrated, the prosthesis (10) has three alternative configurations, one being a front actuator configuration, another being a rear actuator configuration and the other being an inverted actuator configuration. The front actuator configuration is preferred. FIGS. 1 to 7 show the prosthesis (10) with the front actuator configuration while FIGS. 8 to 13 show the prosthesis (10) with the rear actuator configuration.

FIGS. 15 to 21 show the inverted actuator configuration.

Front Actuator Configuration

Figure 1:
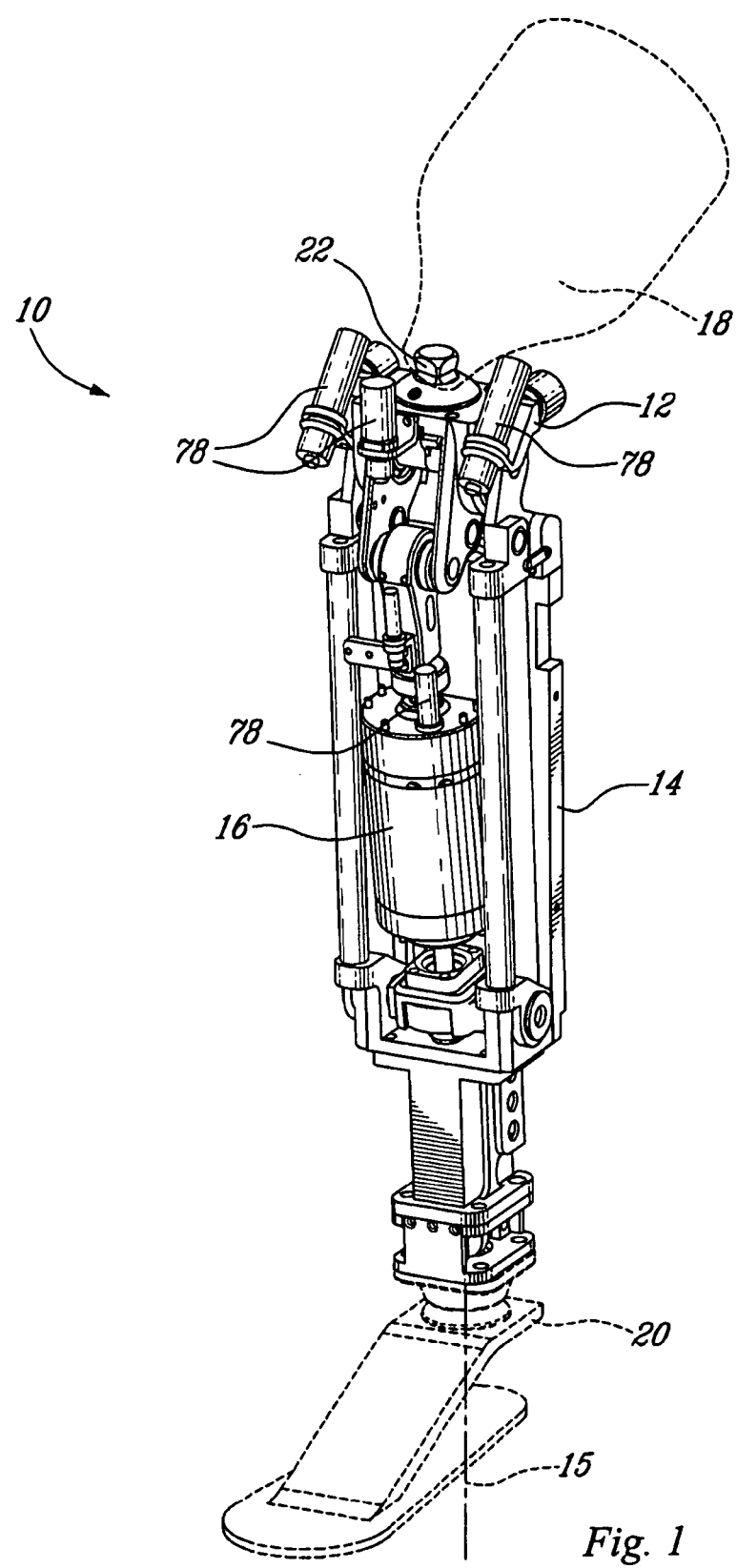
FIG. 1 is a perspective view of an actuated prosthesis with a front actuator configuration.
Figure 2:
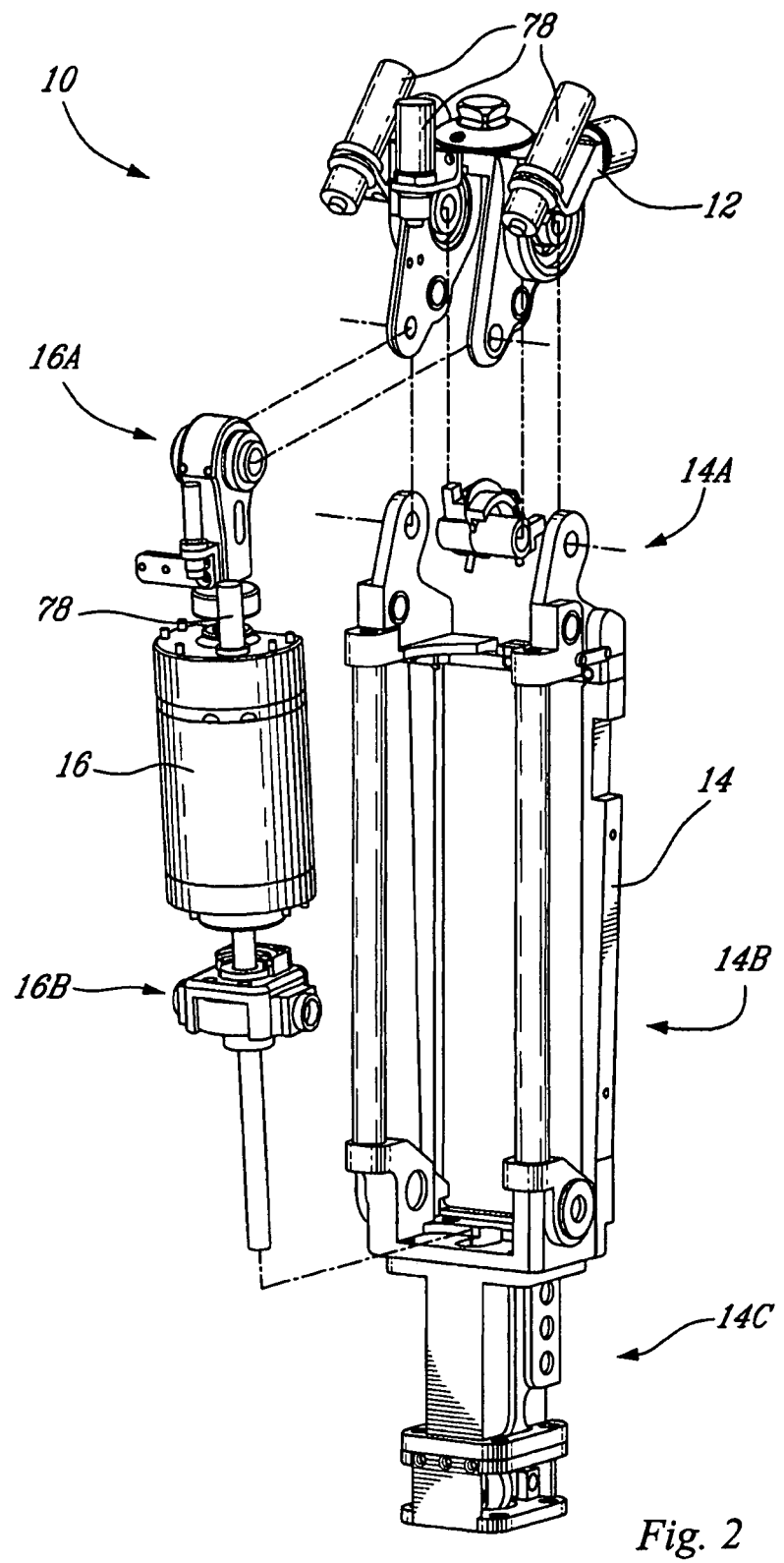
FIG. 2 is a partially exploded perspective view of the prosthesis shown in FIG. 1.

FIGS. 1 and 2 show the basic components of the prosthesis (10), which include a primary joint referred to as a knee member (12), an elongate structural member referred to as an elongated trans-tibial member (14), and a linear actuator (16) acting between the knee member (12) and the trans-tibial member (14) to cause relative movement between them. The prosthesis (10) also comprises a socket connector assembly (17) for connecting a socket (18) on the knee member (12) and a connector assembly (19) for connecting to a terminal portion of a limb such as an artificial foot (20) under a bottom end of the trans-tibial member (14).

The socket (18) must achieve adequate effort transfers between the prosthesis (10) and the amputee's stump. The design of the socket (18) is usually a custom operation in order to achieve an optional load transmission, stability and efficient control for the stump's mobility. The socket (18) is generally held in place on the stump of the user by a suction effect created by an appropriate system such as, for example, a flexible suction liner of type "Thermolyn" manufactured by the Otto Bock Inc. The prosthesis (10) can otherwise use any suitable sockets available on the market.

The socket assembly connector (17) for connecting the socket (18) may comprise a bottom socket connector (22) provided over the knee member (12). The bottom socket connector (22) is preferably removably connected by means of fasteners, for instance screws or bolts. The exact type of bottom socket connector (22) may vary. An example is a connector having a standard male pyramid configuration, such as male pyramid model 4R54 manufactured by Otto Bock Inc. Another example is the sliding connector with male pyramid model 2054-2 manufactured by Ossur Inc. The socket (18) would then be equipped with a corresponding upper connector which fits over the bottom male connector (22). Other types of connectors may be used as well.

The knee member (12) provides the junction between the socket (18) and the trans-tibial member (14) with at least one degree of freedom in rotation. The knee member (12) range of motion is preferably about 105 degrees, where zero degree is at full extension and 105 degrees is at maximal knee flexion.

Figure 3:
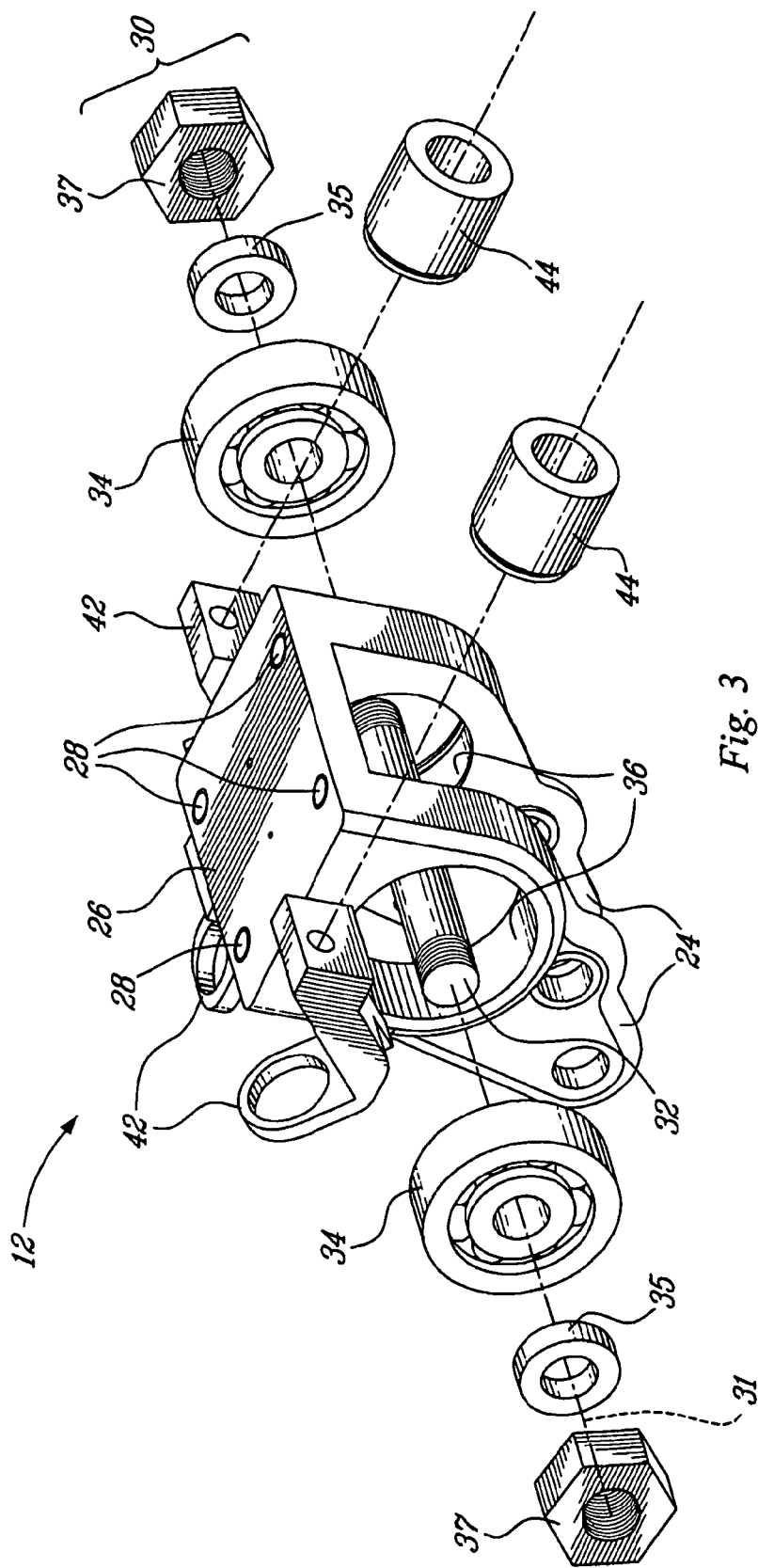
FIG. 3 is an exploded perspective view of the knee member and the first pivot assembly shown in FIG. 1.

FIG. 3 shows an enlarged view of the knee member (12). The knee member (12) is preferably a fork-shaped item, with two flanges (24) projecting from an upper plate (26). The upper plate (26) includes four threaded holes (28) for the removable fasteners of the bottom socket connector (22).

The knee member (12) is connected to the trans-tibial member (14) by means of a first pivot assembly (30). The first pivot assembly (30) operatively connects the trans-tibial member (14) to the knee member (12), thereby making possible a relative rotation between these two parts. It should be noted that the first pivot assembly (30) can also be polycentric. This means that the movement between the knee member (12) and the trans-tibial member (14) is not purely rotational but follows a much more complex pattern. The right and left sides of the parts can further be slightly different, thereby causing a slight torsion movement around a vertical axis. Nevertheless, the general overall movement remains substantially a rotation around a pivot axis.

Figure 4:
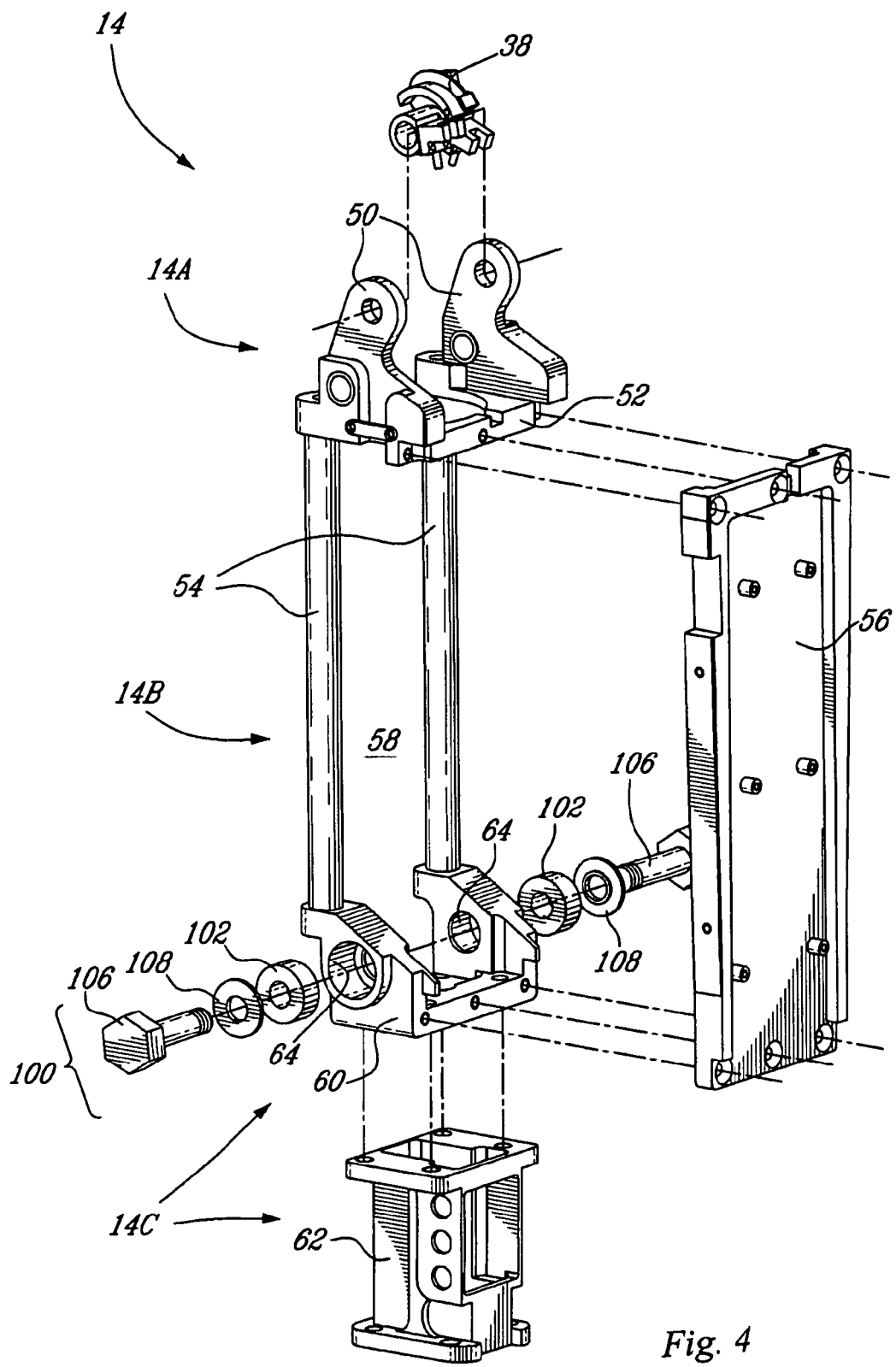
FIG. 4 is an exploded view of the trans-tibial member and the third pivot assembly shown in FIG. 1.
Figure 7:
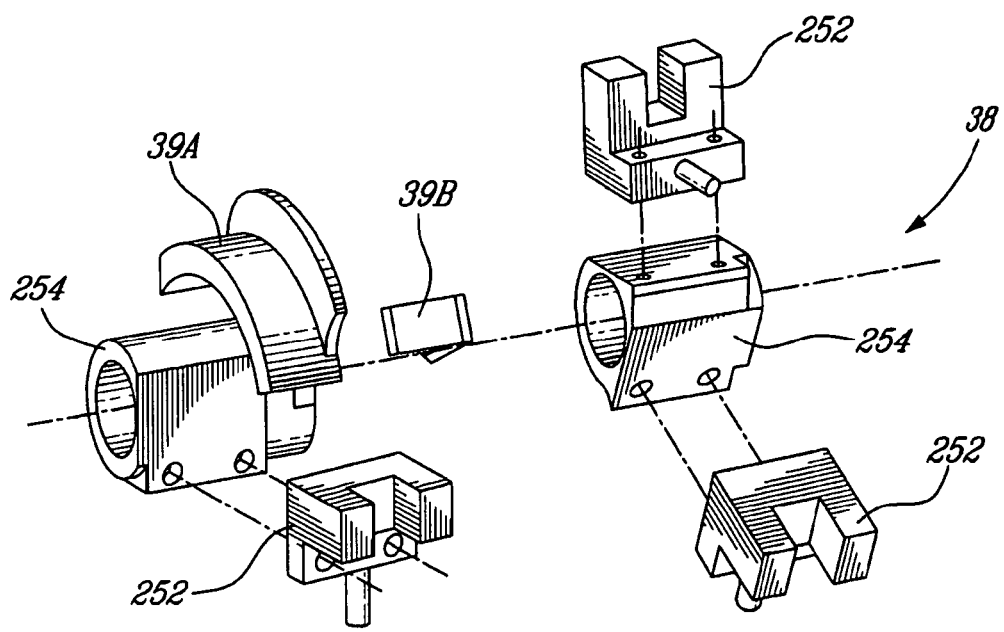
FIG. 7 is an exploded view of the optical switch support shown in FIG. 4.

The first pivot assembly (30) defines a first pivot axis (31) that is substantially perpendicular to a main longitudinal axis (15) extending along the length of trans-tibial member (14) in the frontal plane, as shown in FIG. 1. This first pivot assembly (30) comprises an axle (32) supported by two bearings (34), each mounted in a corresponding housing (36) in the flanges (24) of the knee member (12). An example of bearing (34) is a single groove-bearing model 6300-ZZ manufactured by NSK Inc. Of course, other types of bearings (34) may be used as well. A 10 mm shoulder nut (37) and a set of external spacers (35) retain the bearings (34) on threaded ends of the axle (32). An optical switch support (38), shown in FIGS. 2, 4 and 7, is mounted around the axle (32) between the two flanges (24) of the knee member (12). The support (38) is described later in the description.

Preferably, as best shown in FIG. 3, a set of energy absorption bumpers (44) is provided at the back side of the knee member (12) to prevent out of range motion.

These bumpers (44) can be, for example, bumper model GBA-1 manufactured by Tecspak Inc. Of course, other types of bumpers (44) may be used as well. They are mounted on corresponding brackets (42) located on the side and the front of the upper plate (26) of the knee member (12). The brackets (42) are also used to support connectors (78) which are described later in the description.

As can best be seen in FIG. 4, the trans-tibial member (14) includes three main sections, namely an upper section (14A), a middle section (14B), and a bottom section (14C).

The upper section (14A) of the trans-tibial member (14) is preferably a fork-shaped item with two flanges (50) projecting from a mounting base (52). The mounting base (52) is rigidly connected to a pair of trans-tibial post bars (54). A back plate (56) is provided at the back. The pair of bars (54) and the back plate (56) are part of the middle section (14B). They are both connected to the bottom section (14C), which is itself formed from two parts (60, 62). The first part (60) is a somewhat U-shaped part under which the second part (62) is attached. The second part (62) is an extension under which the artificial foot (20) is provided. The foot connector assembly (19) for connecting the artificial foot (20) includes a set of threaded holes in which screws are inserted. Other types of connectors may be used.

The artificial foot (20) may be, for example, a standard 26 cm Trustep prosthetic foot manufactured by College Park Industries Inc. or Allurion model ALX5260 prosthetic foot manufactured by Ossur Inc. Other types of articulated or non-articulated artificial foot (20) may be used if the selected prosthetic foot provides approximately at least the same dynamical response as the ones mentioned here above. The design of the prosthesis (10) is modular and consequently, it can be adjusted to any morphology. The artificial foot (20) may have an exposed metal or composite structure. It may also have a cosmetic covering that gives it the appearance of a human ankle and foot.

The pair of bars (54) and the back plate (56) provide a space (58) in which most of the actuator (16) is located. The various electronic and electric components may also be attached on either sides of the back plate (56). This compact arrangement keeps the overall dimensions within that of a normal human leg.

Figure 5:
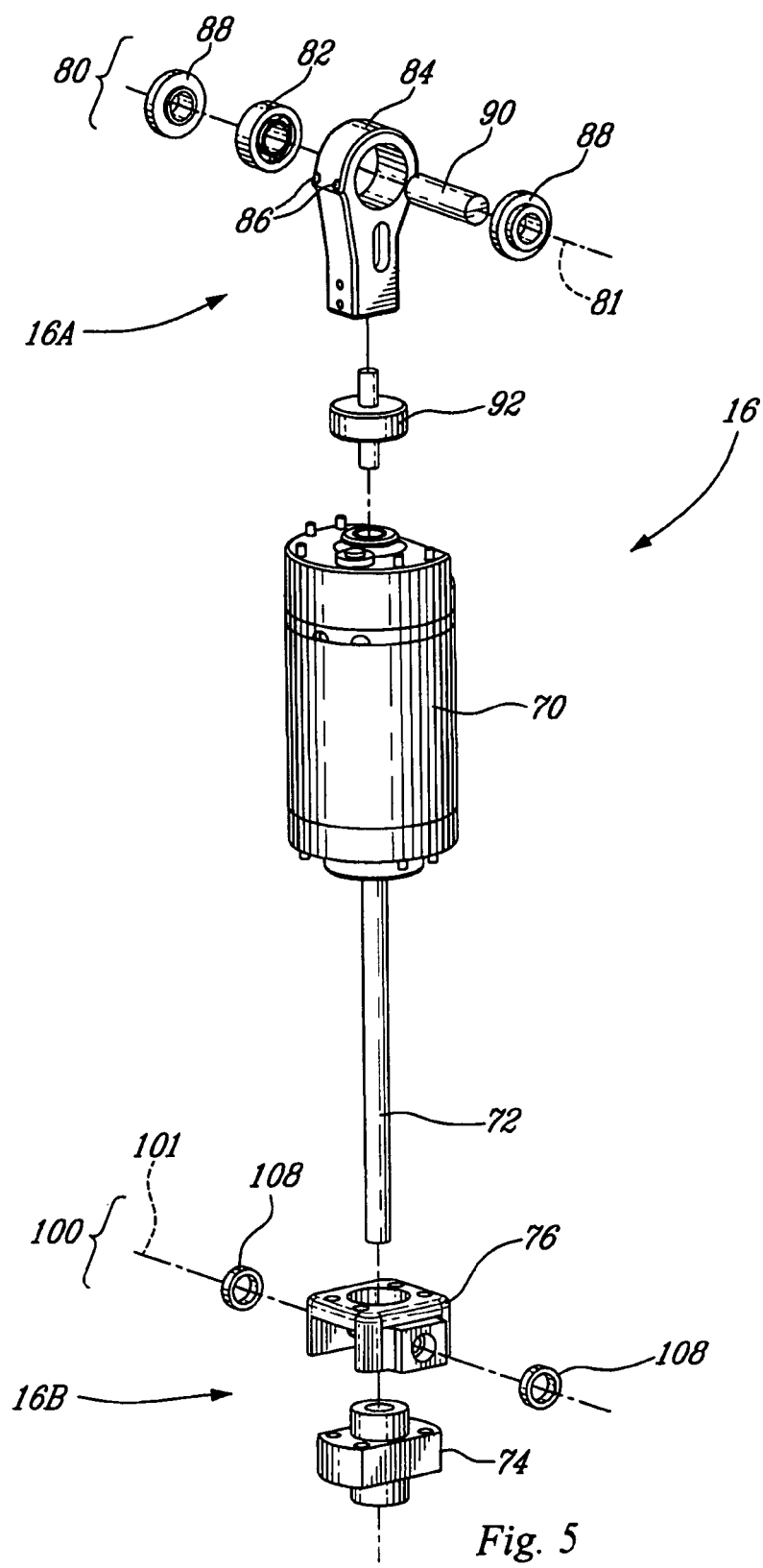
FIG. 5 is a partially exploded view of the linear actuator and the second pivot assembly shown in FIG. 1.

The linear actuator (16) is shown in FIG. 5. The upper end (16A) of the actuator (16) is connected to the knee member (12) by a pivot assembly 80 and the bottom end (16B) is connected to the bottom section (14C) of the trans-tibial member (14). The function of the actuator (16) is to supply the prosthesis (10) with the necessary mechanical energy to execute, in a sagittal plane, the angular displacements synchronized with the amputee's locomotion. The linear motion of the actuator (16) is used to control the angle of the knee member (12) with reference to the trans-tibial member (14). The actuator (16) includes an electrical motor (70) coupled with a mechanism (72, 74) to transfer rotational motion into linear motion. An example of motor (70) is the model BN2328EU manufactured by Poly-Scientific. The motor (70) operates a screw (72) engaged to a fixed follower (74) at the bottom of the actuator (16). The follower (74) is held by a follower support (76). The follower (74) and the follower support (76) constitute the bottom end (16B) of the actuator (16). In use, when the motor (70) rotates, the screw (72) is rotated in or out of the follower (74). This pushes or pulls the knee member (12), thereby causing a relative rotation between the knee member (12) and the trans-tibial member (14).

The choice of the linear actuator (16) is primarily based on weight versus torque ratio and speed of available motor technologies. It is preferred over a direct drive system coupled directly to the knee member (12) because it takes less space for the torque requirement in human locomotion. It was found that ideally, the actuator (16) must be capable of supplying a continuous force of about 515 N and a peak force of about 2250 N.

Figure 6:
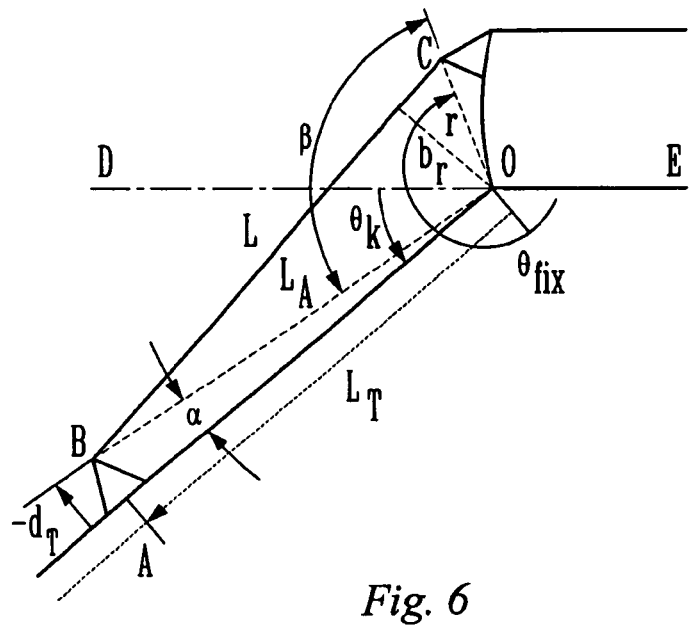
FIG. 6 is a diagram illustrating the geometrical model with the front actuator configuration.

The second pivot assembly (80) operatively connects the upper end (16A) of the actuator (16) to the knee member (12). The second pivot assembly (80) defines a second pivot axis (81) that is substantially parallel to the first pivot axis (31). It is also spaced from the plane defined by its first pivot axis (31) and the main longitudinal axis (15). An example of this configuration is schematically illustrated in FIG. 6. This diagram represents the various pivot axes. The first pivot axis (31) is identified as "O". The second pivot axis (81) is identified with the letter "C". Both axes (C, 0) are spaced apart by the distance "r". This distance creates a lever arm allowing the actuator (16) to move the trans-tibial member (14) with reference to the knee member (12).

FIG. 5 shows that the second pivot assembly (80) comprises a bearing (82) inserted in a mechanical connector (84) forming the upper end (16A) of the actuator (16). The bearing (82) may be a needle bearing, for example needle bearing model NK14/16 manufactured by INA Inc. It is held in place by means of shoulder screws (86) and aluminum spacers (88). It was found that ideally, the bearing (82) must withstand a static charge up to about 11500 N (2600 lbf) and allows for a typical misalignment of 1 to 3. The needle bearing (82) is preferred since it has practically no mechanical play and a low coefficient of friction when compared to bushing or rod ends. Of course, other types of bearings may be used as well. An axle (90) links the mechanical connector (84) to corresponding holes in the flanges (24) of the knee member (12). The mechanical connector (84) is secured over the motor (70) using a load cell (92), which is described later in the description.

The bottom end (16B) of the actuator (16) is operatively connected to the trans-tibial member (14) using a third pivot assembly (100), as shown in FIGS. 4 and 5. The third pivot assembly (100) defines a third pivot axis (101) and also preferably comprises one or more needle bearings (102), each mounted in a corresponding housing (64) provided in the first part (60) of the bottom section (14C) of the trans-tibial member (14). Two standard needle bearings (102) may be used for that purpose, for example needle bearing model NK14/16 manufactured by INA Inc. Of course, other types of bearings may be used as well in the second (80) and the third pivot assembly (100). A set of screws (106) and spacers (108) completes the third pivot assembly (100).

The various structural parts of the prosthesis (10) are preferably made of a light material, for instance aluminum or a composite material, such as carbon fiber, fiberglass or the like. A particularly suitable material is thermally treated 6061T6 aluminum. The various parts are preferably screwed together, although they may be welded and otherwise secured together Screwing the parts together is preferred since this increases manufacturability, facilitates servicing and replacement of the parts, and usually improves the overall aesthetics.

FIG. 7 shows the specialized mechanical support (38) appearing in FIGS. 2 and 4. This specialized mechanical support (38) is used firstly to fix the optical switches as explained hereafter. Secondly, the specialized mechanical support (38) is used to facilitate the transition between the part of a cable (not shown) between the relatively fixed section of the prosthesis (10) and the relatively movable section thereof.

Connectors (78), attached to the brackets (42) of the knee member (12), provide the required connections. A similar connector (78) is provided on the motor (70). A two-part wire clamp (39A, 39B) on parts (254) allows to hold the wire on the support (38).

Control System

Figure 14:
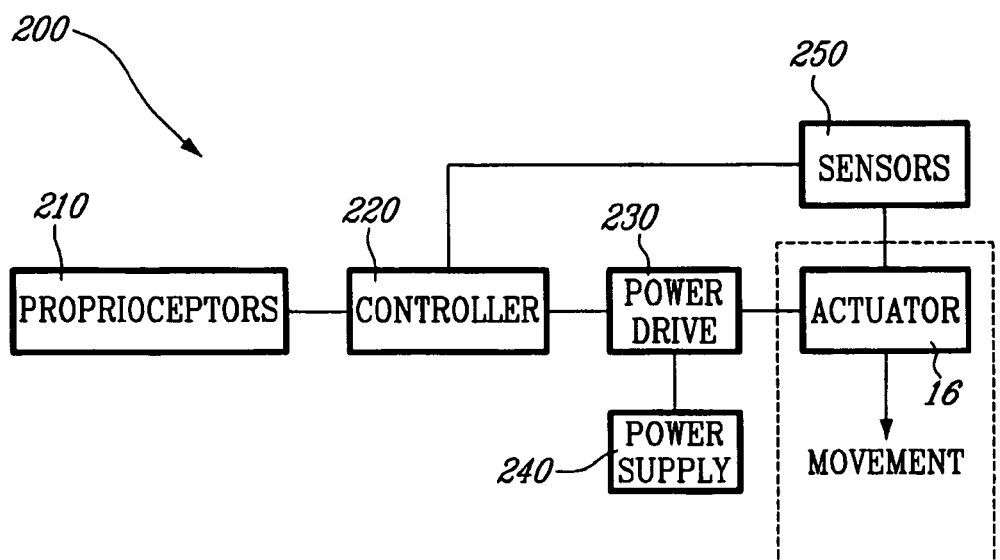
FIG. 14 is a bloc diagram showing an example of a control system for the actuator of the prosthesis.

The actuator (16) shown in the prosthesis of FIGS. 1 to 7 is controlled by the control system (200) shown in FIG. 14. This figure first shows a set of artificial proprioceptors (210), which are sensors used to capture information in real time about the dynamics of the amputee's locomotion. The set of artificial proprioceptors (210) provide sensing information to a controller (220). The controller (220) determines the joint trajectories and the required forces that must be applied by the actuator (16). The set-point (joint trajectories and the required forces) is then sent to the actuator (16) via the power drive (230) itself connected to the power supply (240).

The power supply (240) can be, for example, a flexible battery pack belt such as the Lighting Powerbelt model, manufactured by Cine Power International Ltd. Other examples of power supply (240) are the battery model SLPB526495 manufactured by Worley Inc. and the super capacitors manufactured by Cap-XX. Examples of power drive (230) are the 5121 model, manufactured by Copley Controls Corps Inc. and the model BE40A8 manufactured by Advanced Motion Control. It should be noted that the design of the power supply (240) and that of the power drive (230) are not limited to the devices mentioned here above and could be performed by any custom or commercial products if the selected devices meet the electrical specification of the selected actuator (16) used with the prosthesis (10).

Preferably, the prosthesis (10) further includes a set of sensors (250) to provide feedback information to the controller (220). This feedback allows the controller (220) to adjust the forces and various other parameters. Examples of parameters that can be monitored are the relative angle of the knee member (12) and the torque at the knee member (12) being exerted by the actuator (16). Other types of measurements may be taken. The measurement of the relative angle of the knee member (12) can be taken, for example, by a standard commercially available incremental optical encoder (260) such as a reading head model EM1-0-250 and a Mylar® strip (262) marked with evenly spaced increments model LIN-250-16-S2037 manufactured by US Digital Inc. Others sensors used as limit switches for the limitation of the angular motion of the prosthesis (10) are the optical switches preferably mounted onto the specialized mechanical support (38). Cable connectors (78), shown in FIGS. 1 and 2, allow to link the external devices to internal components of the prosthesis (10).

The optical switches (252) are fixed on the first pivot axis (31) and are used to set the reference angular position of the knee member (12). Once this reference position is known, the optical encoder information is used to compute the knee member (12) angle via motor rotation, roller-screw pitch and prosthesis geometry. Moreover, the optical switches (252) are used to prevent out of range motion by sending a signal to the controller (220) when the knee member (12) approaches critical positions. Of course, the optical switches (252) may be use for other purposes according to the nature of the command associated with the switches detection. Another possible way of measuring the relative angle of the knee member (12) is by using a combination of an absolute optical encoder such as, for example, encoder model E2-512-250-i manufactured by US Digital Inc. and optical switches. An example of these switches is the switch model PM-L24 manufactured by SUNX.

The measurement of the torque is taken from the force being exerted by the actuator (16) measured by a load cell (92). An example of the load cell is the model LC 202 1 K manufactured by Omegadyne. A connector on the motor (70) links the internal sensor to the cable. It should be noted that the sensors (250) of the prosthesis (10) are not limited to the above-mentioned devices and can be performed by other suitable instruments.

Operation of the Front Actuator Configuration

In operation, the knee assembly (12) is connected to the socket (18) and the pivot assembly (30) permits relative motion between the trans-tibial member and the knee about a generally transverse horizontal axis. Rotation of the knee member relative to the trans-tibial member (14) is controlled by operation of the actuator (16). The actuator (16) acts between the pivot assembly (80) on the knee member (12) and the pivot assembly (100) at the lower end of the trans-tibial member (14) so that changes in the length of the actuator (16) will cause a corresponding rotation about the pivot (30).

The length of the actuator (16) is adjusted by control signals from the controller (220) that supplies power to the motor (70) to rotate the screw (72) in one direction or the other. Rotation of the screw (72) causes the follower (74) to move along the screw (72) and this motion is transferred through the connection provided by the pivot assembly (100) to the trans-tibial member (14). This causes a corresponding rotation of the knee member (12) and trans-tibial member (14) about the pivot axis (30) to provide the desired motion. Obviously the rate and extent of rotation may be adjusted through control signals to the motor (70) and the sensors embodied in the prosthesis provide the feedback to the controller (220).

Rear Actuator Configuration

FIGS. 8 to 13 show the prosthesis (10) in accordance with a second possible embodiment. This illustrates an example of a prosthesis (10) with a rear actuator configuration. This embodiment is very similar to the one using the front actuator configuration. It is illustrated with another kind of actuator (16) and another model of artificial foot (20). The middle section (14B) of the trans-tibial member (14) uses four bars (54) instead of two. It does not have a back plate. Moreover, no bottom extension is provided on the trans-tibial member (14).

The trans-tibial member (14) also has a shell type architecture composed, for example, of ½" trans-tibial post bars (54) linking together the knee member (12) and the artificial foot (20). In the illustrated embodiment, the actuator (16) could be a standard linear motor (FIG. 5) or a serial elastic actuator (SEA) (FIG. 8) equipped with a customized commercially available motor (70) although the prosthesis (10) is designed such that it can receive any type of linear actuator (16) of the same approximate size. The SEA actuator (16) (FIG. 8) has a ball screw transmission system including a screw (72) coupled with an elastic device (110) of known characteristics. This actuator (16) (FIG. 8) allows a force control actuation based on the deformation of elastic components. As well, the design allows energy storage, shock tolerance and relatively stable force control. The SEA actuator (16) (FIG. 8) was developed by Gill Pratt of the MIT Leg Laboratory and has been patented in 1997 as U.S. Pat. No. 5,650,704. In one implementation, it was provided with a Litton BN23-28 motor (70) and a ⅜" diameter with ⅛" pitch ball screw (72). The SEA actuator (16) (FIG. 8) is commercialized by Yobotic Inc.

Figure 8:
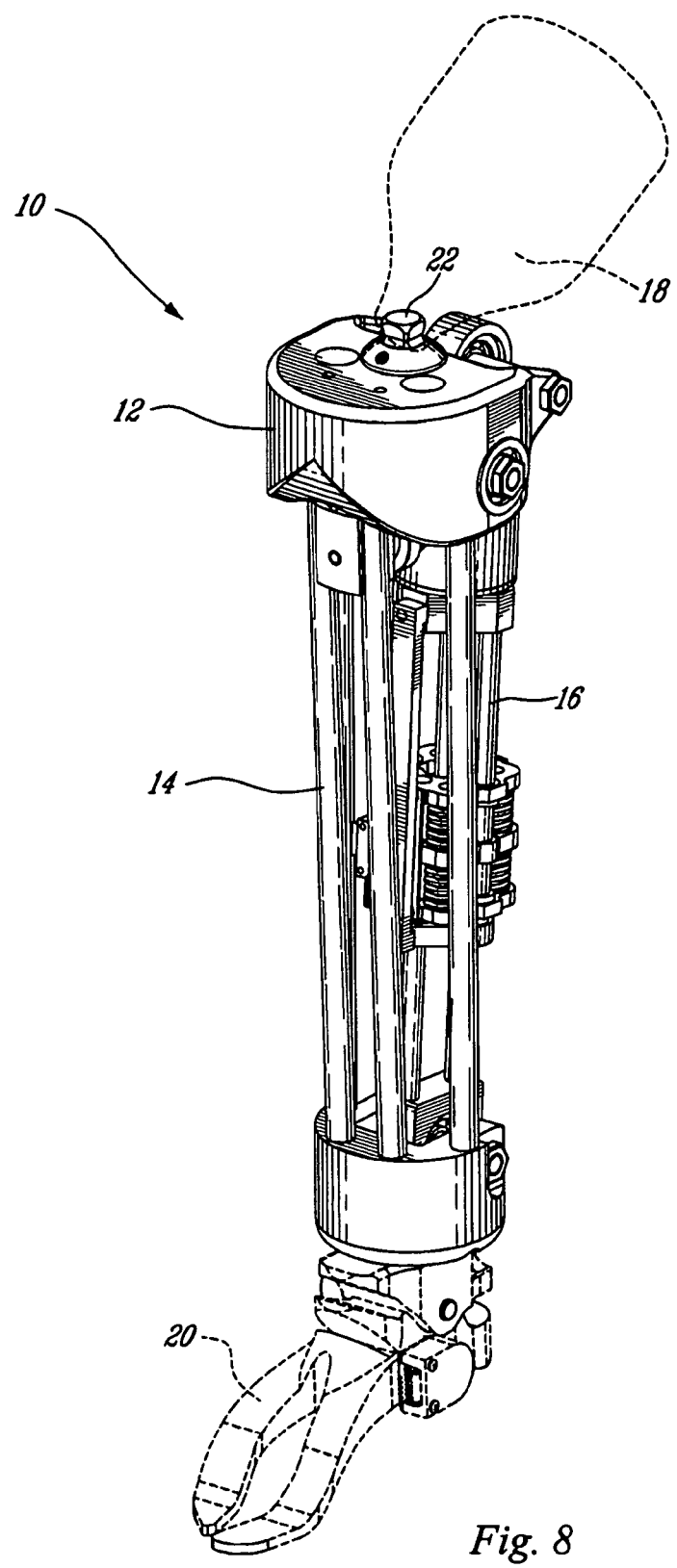
FIG. 8 is a perspective view of an actuated prosthesis with a rear actuator configuration, in accordance with another possible embodiment of the present invention.
Figure 9:
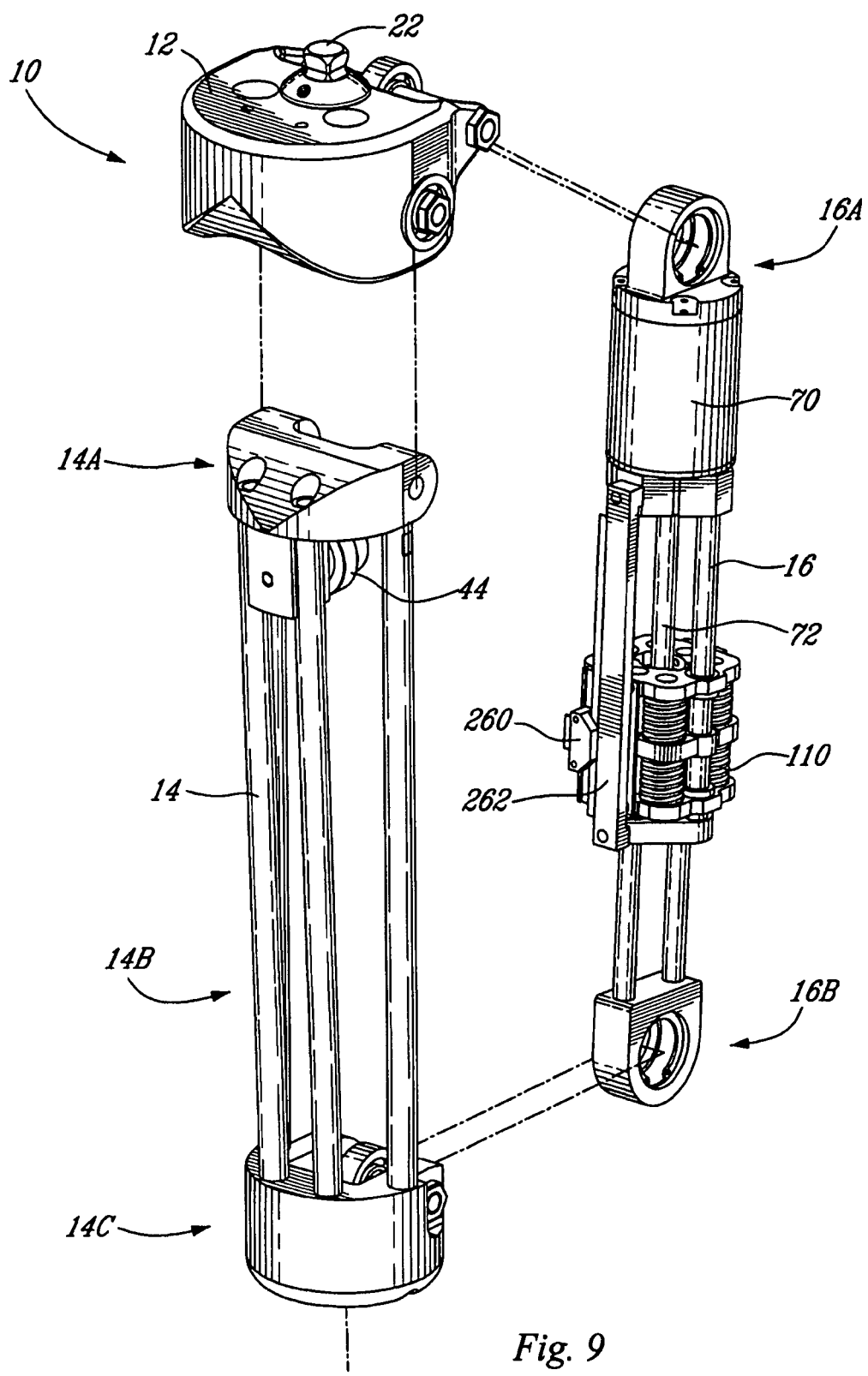
FIG. 9 is a partially exploded perspective view of the prosthesis shown in FIG. 8.
Figure 10:
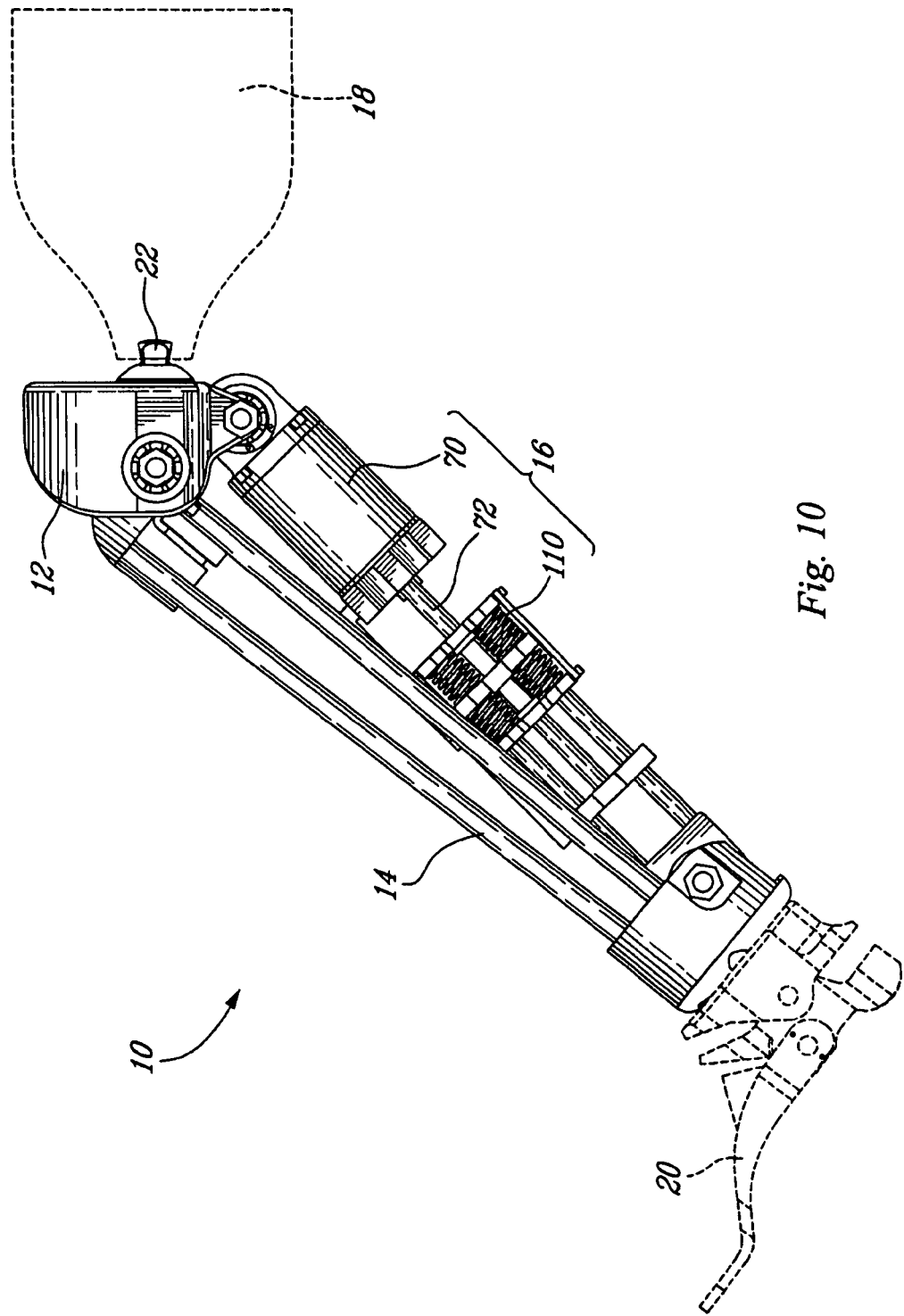
FIG. 10 is a side view of the prosthesis shown in FIG. 8.
Figure 11:
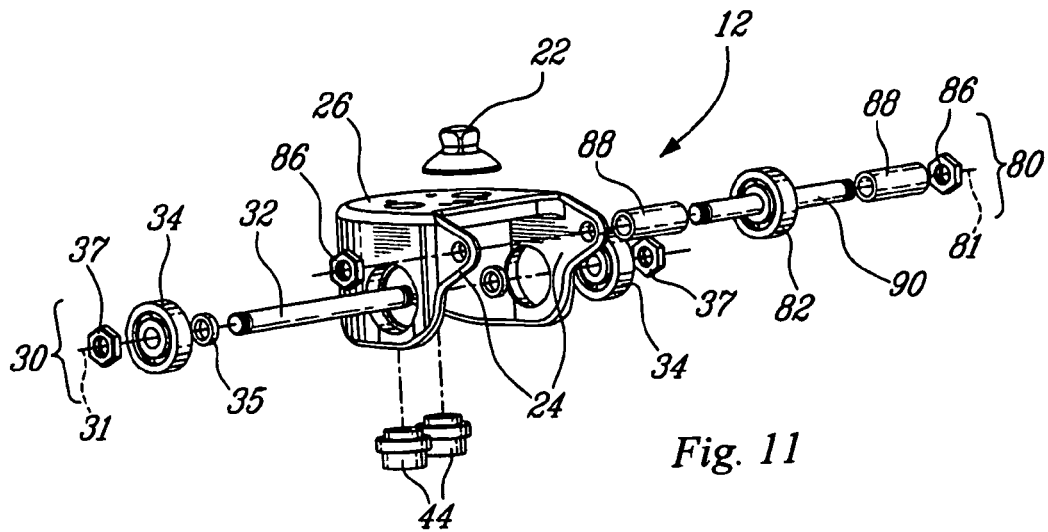
FIG. 11 is an exploded perspective view of the knee member, the first pivot assembly and the second pivot assembly shown in FIG. 8.
Figure 12:
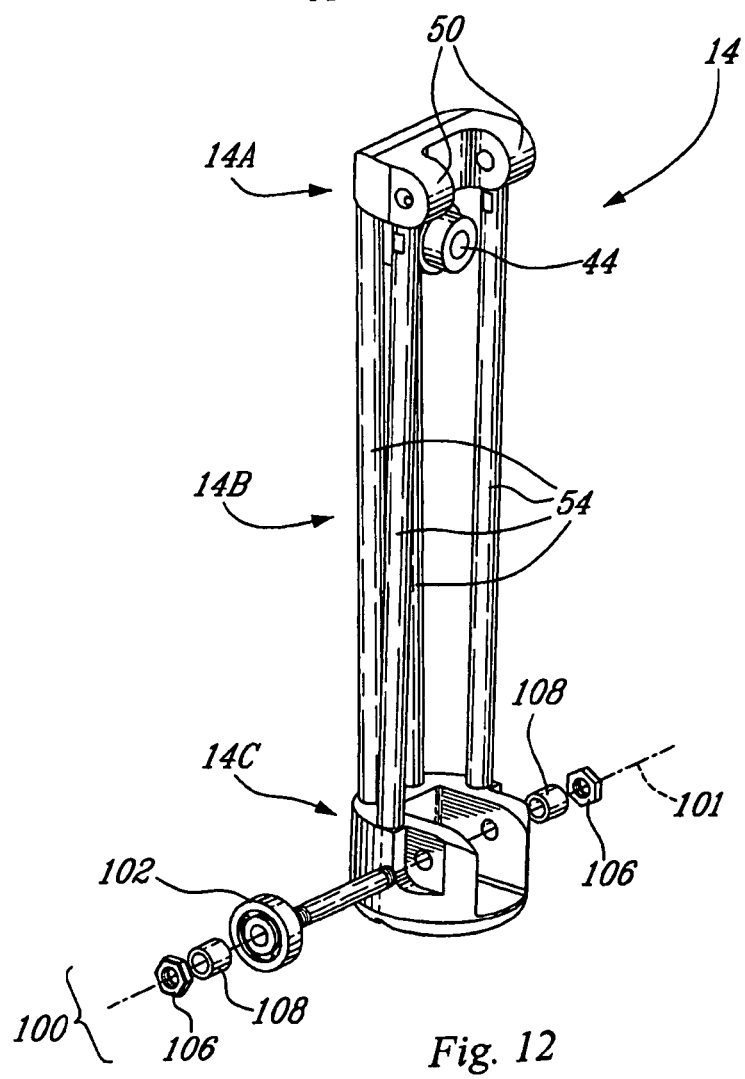
FIG. 12 is a partially exploded view of the trans-tibial member and the third pivot assembly shown in FIG. 8.

In the arrangement shown in FIG. 8, the torque may be measured, for example, by a standard commercially available potentiometer measuring the compression of the elastic devices of the actuator (16) such as the conductive plastic resistance elements model PTN025 manufactured by Novotechnik Inc. The measurement of the angle between the knee member (12) and trans-tibial member (14) can also be computed directly from the measurement of the length of the actuator (16) and the known geometry of the prosthesis. A standard commercially available incremental optical encoder (260), such as reading head model EMI-0-250 is mounted on the moveable part and a Mylar strip (262) marked with evenly spaced increments (model LIN-250-16-S2037 manufactured by US Digital Inc.) is secured to the stationary part. As the motor (70) rotates the drive screw (70), a direct reading of the length of the actuator (16) is thus obtained.

Figure 13:
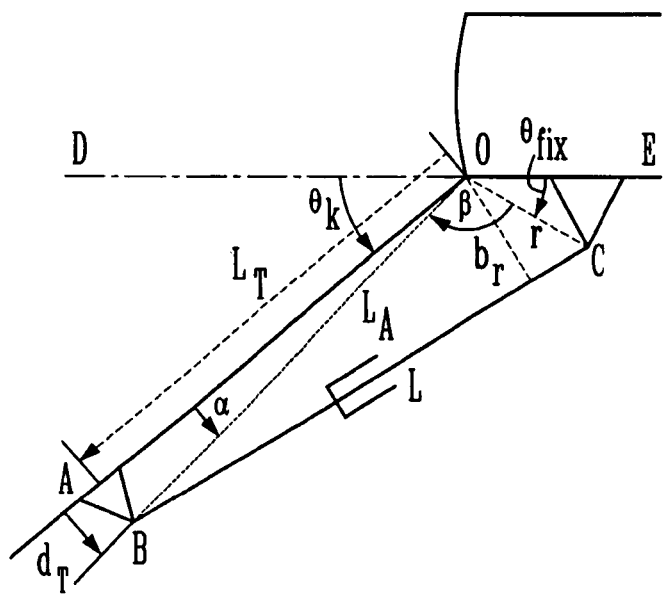
FIG. 13 is a diagram illustrating the geometrical model with the rear actuator configuration.

FIG. 13 illustrates the geometrical model of the rear actuator configuration. It is essentially similar to that of the front actuator configuration as shown in FIG. 6.

Inverted Actuator

In each of the above embodiments, the actuator (16) has been arranged with the motor (70) adjacent to the knee member (12) and the follower (74) extending to the lower, ankle region of the trans-tibial member (14). Such an arrangement simplifies the routing of the power and control lines and generally allows a tapering profile toward the ankle to conform to the natural profile of a leg. However, with these arrangements the motor (70) moves with the pivot assembly (80) through the range of motion of the prosthesis and accordingly the swept volume of the motor must be accommodated in the design of the knee member (12). Similarly, the location of the motor (70) adjacent the knee member causes variations in the mass distribution and hence the dynamics of the prosthesis during movement of the leg which may result in an unnatural feel to the prosthesis in use. To address these considerations a further embodiment of the prosthesis (10) is shown in FIGS. 15 to 21 in which like components will be described by like reference numerals with a prime suffix (') for clarity.

Figure 15:
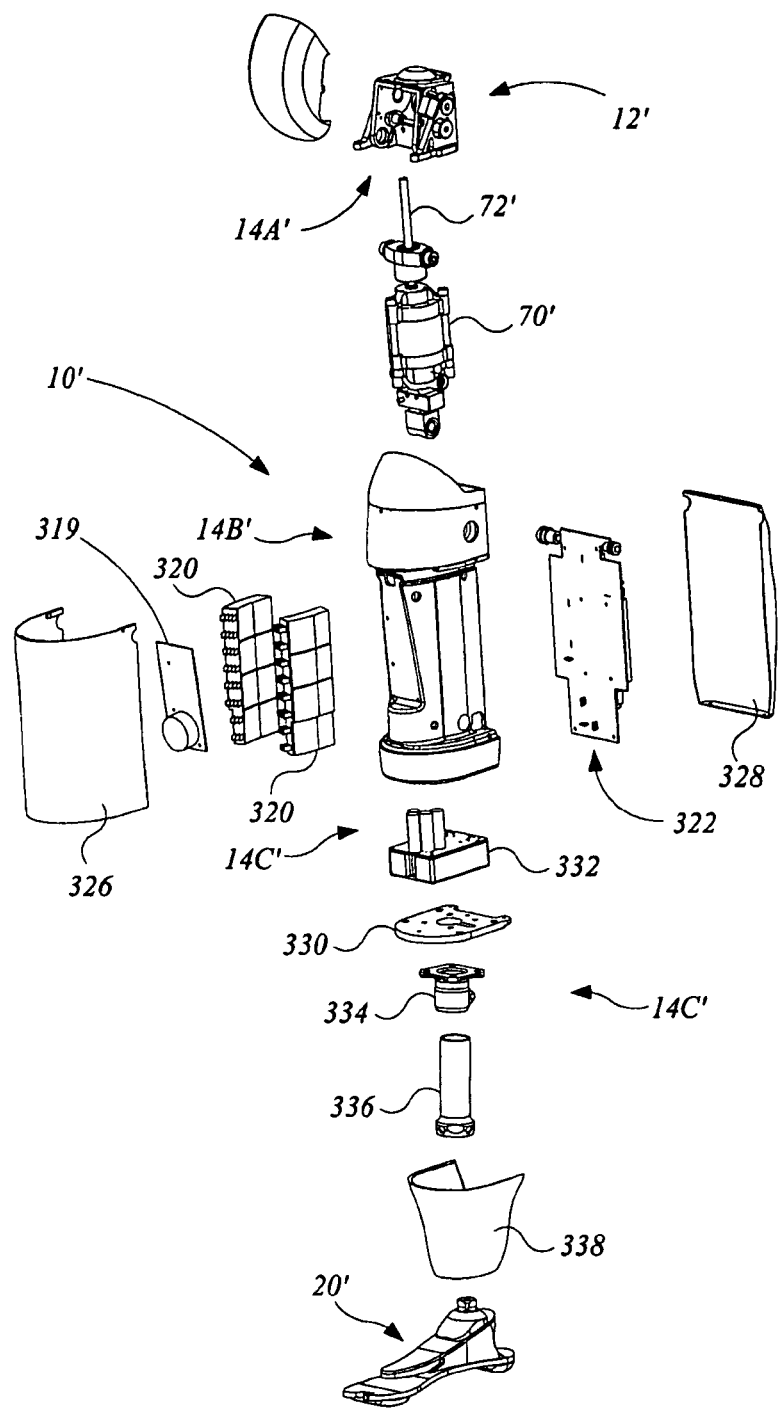
FIG. 15 is an exploded perspective view of a further embodiment of a prosthesis.
Figure 16:
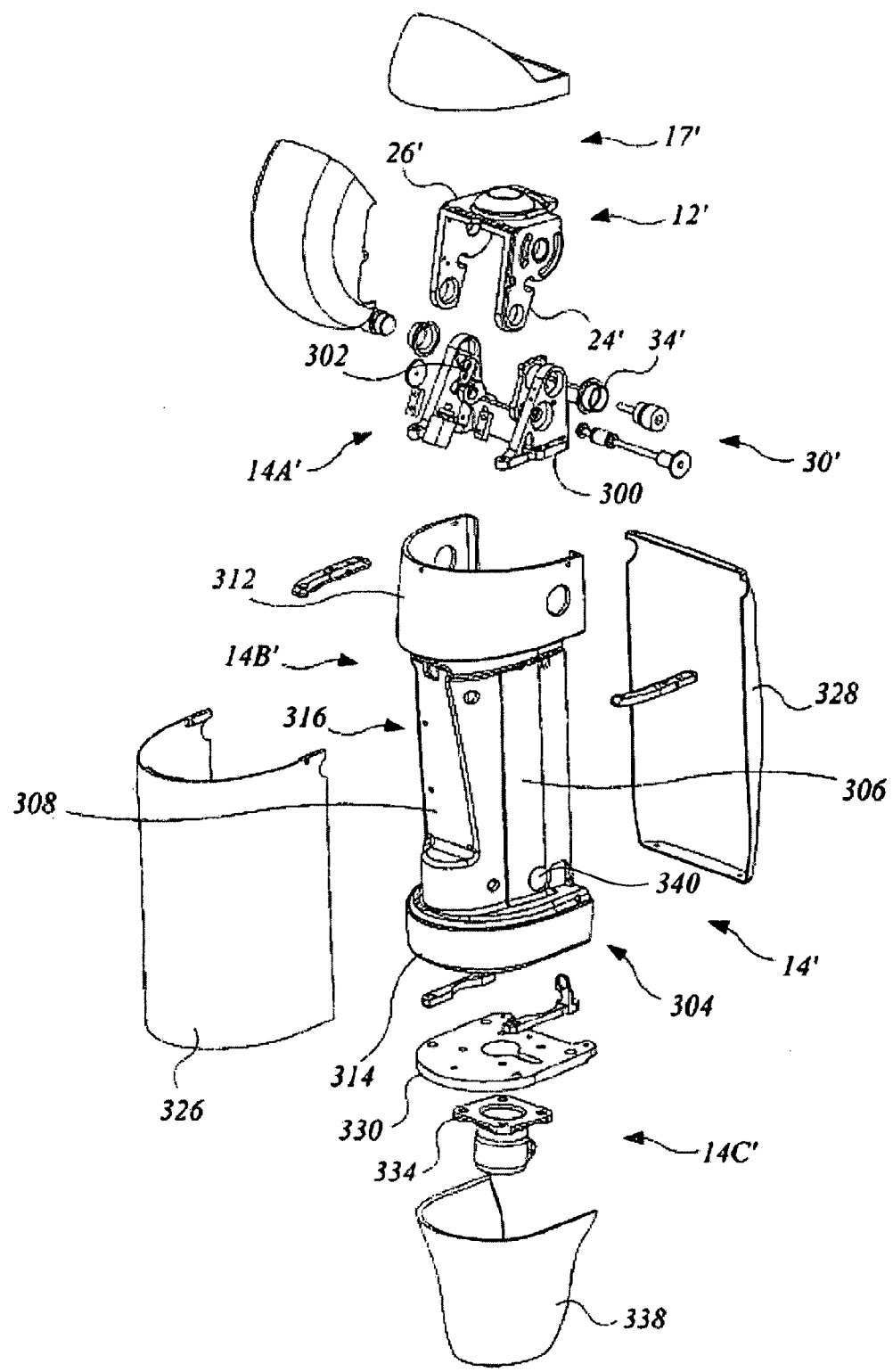
FIG. 16 is a view similar to FIG. 15 on an enlarged scale of structural components of the prosthesis of FIG. 15.
Figure 18:
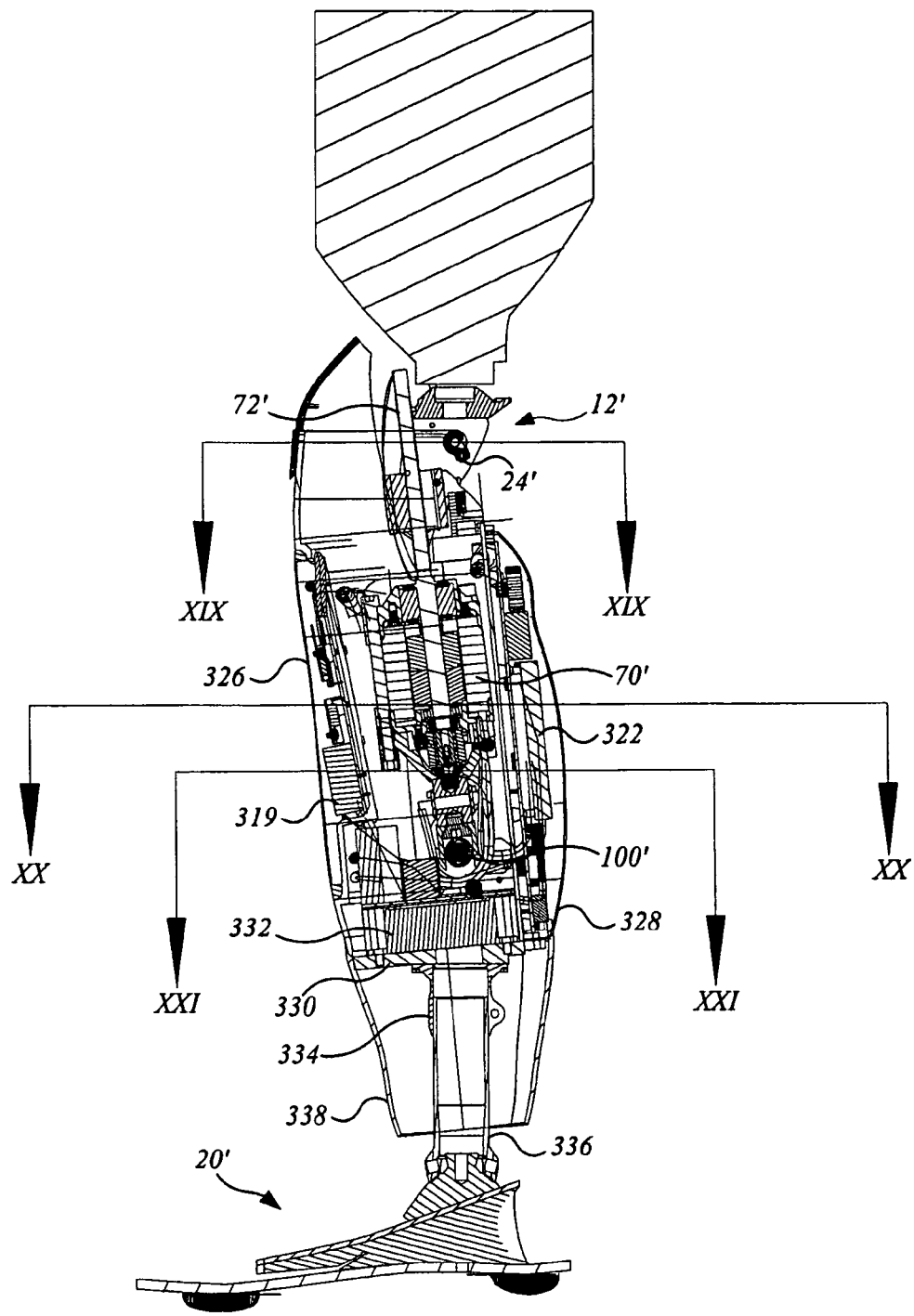
FIG. 18 is a longitudinal side section of the prosthesis of FIG. 15.
Figure 19:
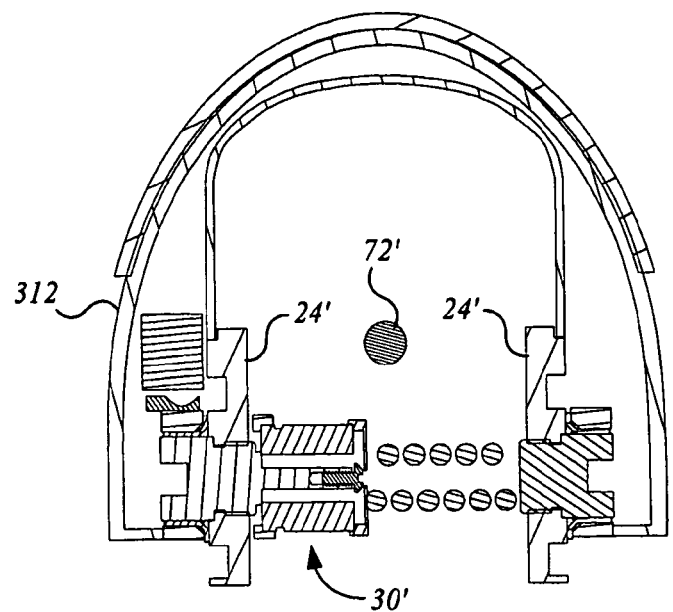
FIG. 19 is a view on the line XIX-XIX of FIG. 18.
Figure 20:
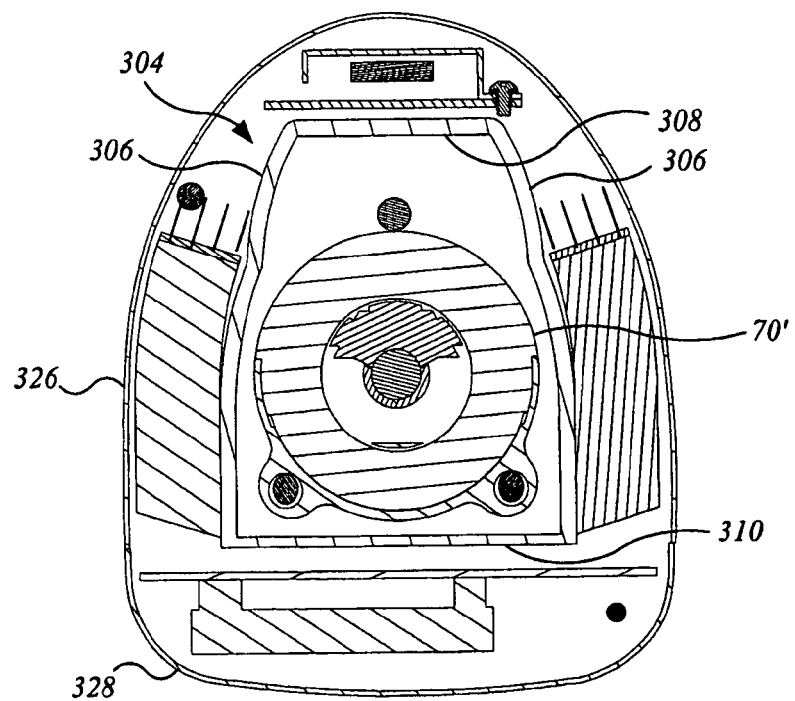
FIG. 20 is a view on the line XX-XX of FIG. 18.
Figure 21:
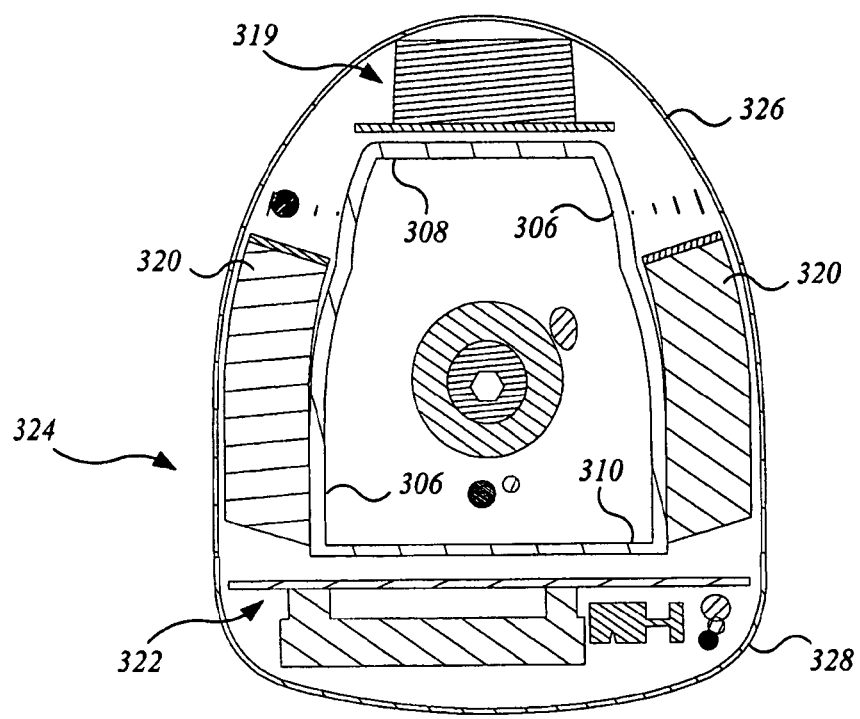
FIG. 21 is a view on the line XXI-XXI of FIG. 18.

Referring therefore particularly to FIGS. 15 and 18, a prosthesis (10') has a knee member (12)' formed as a U shaped member with flanges (24') extending from the upper plate (26'). The lower ends of the flanges (24') receive respective bearings (34') forming part of the pivot assembly (30') that connects the knee member (12') to the trans-tibial member (14'). A socket connector assembly (17') is secured to the upper plate (26') for connection to an appropriate socket.

The trans-tibial member (14') has an upper section (14A') formed by a pair of spaced webs (300) with bores (302) to receive the bearings (34') of the pivot assembly (30'). The webs (300) are secured to shoulders, not shown, at the upper end of the middle section (14B'). The middle section (14B') is formed as an open channel member (304) with laterally spaced side walls (306) interconnected by an integrally formed front wall (308). The channel member (304) is closed by a back wall (310), which is removable to permit access to the interior of the channel member (304). The middle section (14B') thus provides a lightweight structural member of high torsional and bending strength to meet the loading placed upon it.

The upper and lower ends (312, 314) respectively of the channel member (304) are enlarged to receive the upper section (14A') and lower section (14B') and thereby define a waisted intermediate portion (316). The side walls (306) in the waisted portion (316) have generally planar flanks that support energy storage modules (320), typically battery packs, on either side of the channel member (304). The front wall (308) is also formed with a planar facet (314) to receive a control board (319) associated with the operation of the actuator (16') and to regulate power flow to and from the energy storage modules (320).

The back wall (310) also serves as a mounting point for a further control board (322) utilized in the control of the actuator (16'). An external shell (324), formed from front and rear sections (326, 328) respectively, encompasses the intermediate portion (316) and is supported on the enlarged upper and lower ends (312, 314). The shell (324) protects the components mounted on the waisted intermediate portion (316) as well as being contoured to conform to the appearance of a human leg.

The lower section (14C') of the trans-tibial member (14') includes a mounting plate (330) received within the enlarged lower end (314). The plate (330) is bolted the lower ends (314) of the channel member (304) and to the power drive (322) utilized in the control of the actuator (16') which in turn is secured to the middle section (14B)'. A socket (334) is mounted on the underside of the plate (330) to receive a tubular member (336) of the foot connector assembly (20'). The tubular member (336) extends to a male socket formed on the foot (20') and its length may be adjusted to tailor the prosthesis to a particular individual. A skirt (338) extends around the tubular member (336) for cosmetic considerations.

Figure 17:
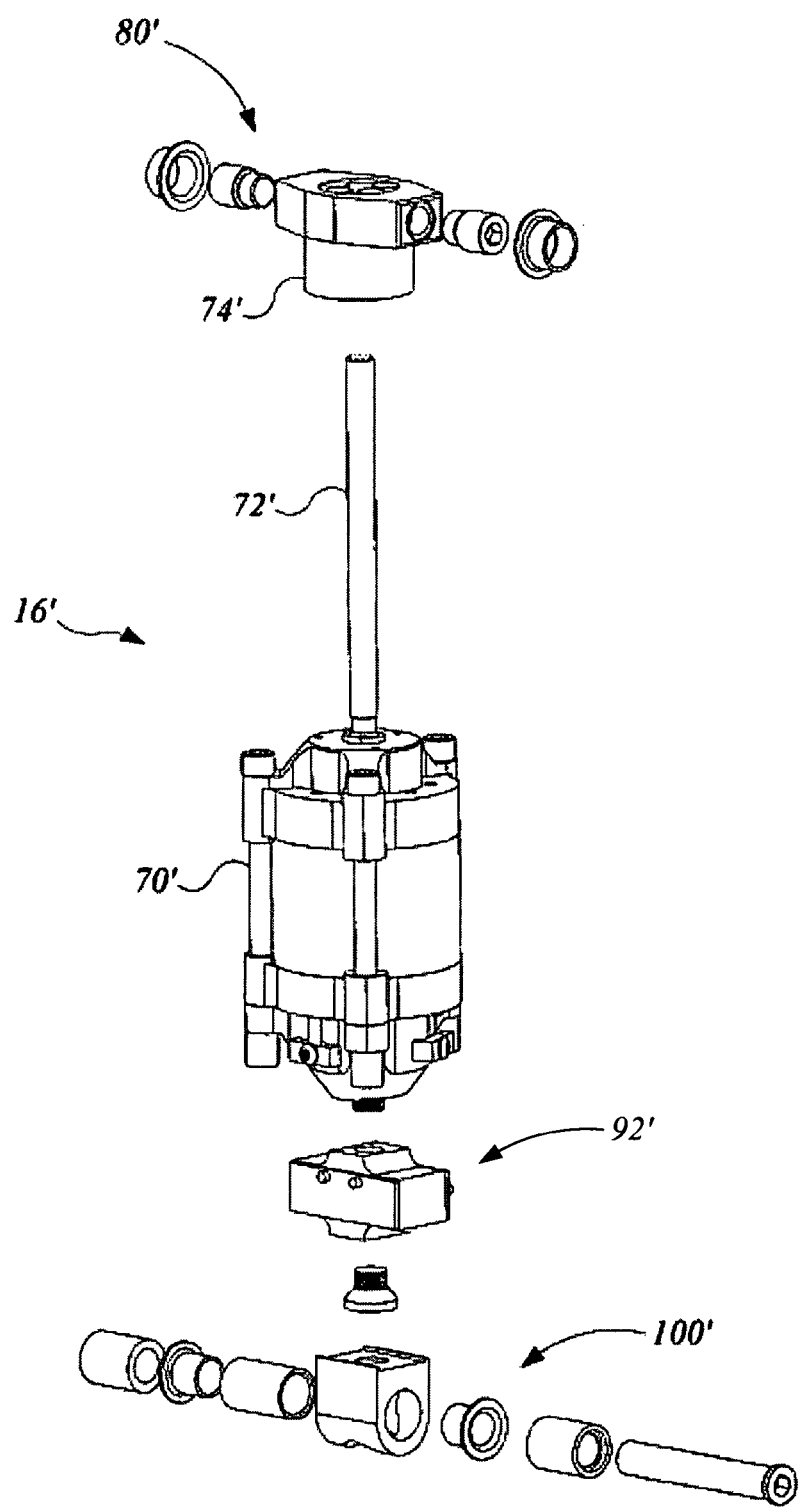
FIG. 17 is a view similar to FIG. 15 on an enlarged scale of the motive components of the prosthesis of FIG. 15.

As can best be seen in FIGS. 15 and 17, the actuator (16') includes a motor (70') with a screw (72)'. The actuator (16') is located within the interior of the middle section (14B') so as to be surrounded by the walls (308, 310, 312), with the screw (72') extending beyond the upper end (312) and between the flanges (26') of the knee member (12'). The screw (72') engages a follower (74') forming part of the pivot assembly (80') that is connected to the knee member (12') at a location spaced from the pivot assembly (30').

The motor (70') is similarly connected through a pivot assembly (100') to the lower end (314) of the middle section (14B') at mounting points (340) (FIG. 16) that receive the bearings of the pivot assembly (100').

Operation of Inverted Actuator

The operation of the inverted actuator is essentially the same as that of the front mounted actuator with rotation of the motor (70') causing a change in the effective length of the actuator (16') and a corresponding rotation of the knee member (12') relative to trans-tibial member (14'). During such rotation it will be noted that the motor (70') swings about its pivot assembly (100') but does not translate along the axis of the prosthesis (10'). The swept volume of the motor through the range of movement is thus reduced allowing better utilization of the space available. It will also be noted that the mass distribution in the prosthesis remains substantially uniform in view of the lack of translation of the motor to provide a more natural feel to the operation of the prosthesis.

The integration of the energy module and control boards on the middle section also provides a more self contained unit and simplifies the routing of the control and power transmission.

EXAMPLE

Calculation for the Optimal Angle

One can assume the following technical specifications:
a geometrical volume corresponding to the anthropometrical volume of a natural shank of an individual having a weight of 70 kg and a height of 170 cm;
a maximal distance r set at 0.055 m, that is r<0.055 m;
a minimal and a maximal length $L_T$ set at 0.3 m and 0.4 m respectively, that is 0.3 m<$L_T$<0.4 m; and
a minimal and a maximal distance $d_T$ set at −0.015 m and +0.015 m, that is −0.015 m<$d_T$<+0.015 m.

The geometrical model can be defined with the following equations:

$$\beta = \pi - \theta_{fix} - \alpha - \theta_K \qquad \text{Equation 1}$$

$$L_A = \sqrt{L_T^2 + d_T^2} \qquad \text{Equation 2}$$

$$\alpha = \arctan\left(\frac{d_T}{L_T}\right) \quad \text{Equation 3}$$

$$L^2 = L_A^2 + r^2 - 2 \cdot L_A r \cdot \cos\beta \quad \text{Equation 4}$$

$$b_r = \frac{r \cdot L_A \cdot \sin\beta}{\sqrt{L_A^2 + r^2 - 2 \cdot L_A \cdot r \cdot \cos\beta}} \quad \text{Equation 5}$$

where $\theta_K$ Knee angle, $\angle DOA$ r Distance between the center of rotation "O" of the knee member (12) and the attachment point of the actuator (16) on the knee member (12)

$\theta_{fix}$ Angle between r and the stump's center axis, $\angle EOC$ $L_A$ Distance between the center of rotation of the knee member (12) and the attachment point of the actuator (16) on the trans-tibial member (14) $\overline{OB}$ $L_T$ Length between the center of rotation of the knee member (12) and the attachment point of the trans-tibial member (14) $\overline{OA}$ $d_T$ Distance between the center axis of the trans-tibial member (14) and the actuator (16) attachment point of the trans-tibial member (14), $\overline{AB}$ $\alpha$ Angle formed between $L_T$, $L_A$: $\angle AOB$ L Length of the actuator (16), $\overline{BC}$ $\beta$ Angle formed between $L_A$, r: $\angle BOC$ $b_r$ Lever arm of the actuator (16) versus the first pivot axis (31)

Preferably, the lever arm $b_r$ is assumed to be maximum at a knee angle $\theta_k$ of 35 degrees. The geometrical calculation of the mechanical design are based on the setting of the distance r, the length $L_T$, the distance $d_T$ and the angle $\theta_{fix}$. Therefore, these parameters are defined in accordance with the anthropomorphic measurements of the amputee and the selected actuator (16).

For an angle $\theta_{fix}$, the optimal value for a maximum lever arm $b_r$ is found when Equation 5 is at a maximum value, that is:

$$\frac{\partial b_r}{\partial \theta_{fix}} = 0 \quad \text{Equation 6}$$

where $\theta_{fix} = \pi - \pi - \theta_K - \beta$.

This condition is reached for the configuration shown in FIGS. 6 and 13 when:

$$\beta = \pm \frac{3}{2}\pi \quad \text{Equation 7}$$

From Equation 1, the optimal angle between distance r and the center axis of the socket, denoted $\theta_{fix}|_{optimal}$, is defined as:

$$\theta_{fix}|_{optimal} = \begin{bmatrix} +\pi/2 \\ -\pi/2 \end{bmatrix} - \theta_k - \alpha \quad \text{Equation 8}$$

where $+\pi/2$ and $-\pi/2$ correspond to the rear and the front actuator configuration respectively.

The result is that the optimal angle $\theta_{fix}$ is preferably set at 125±3 degrees.

It will be appreciated that alternative dimensions and parameters would apply to other limbs such as an arm but the adaptation of the basic components described above to such an environment could readily be made once the underlying concepts are understood.

What is claimed is:

1. An actuated knee joint prosthesis, the knee joint prosthesis comprising:
   a proximal connection member configured to operatively connect the knee joint prosthesis to an amputee;
   an actuator assembly comprising a first end, a second end, a powered actuator, and a mechanical elastic member spaced from the powered actuator, the powered actuator and the mechanical elastic member being positioned in series between the first and second ends, the actuator assembly being operatively connected to the proximal connection member at the first end at a position generally corresponding to that of a knee joint, the mechanical elastic member configured for shock absorption caused by the motion of the knee joint prosthesis, the mechanical elastic member and the powered actuator being located distally from the knee joint;
   a tibial member operatively connected to the second end of the actuator assembly and rotatably connected to the proximal connection member at least by the actuator assembly; and
   at least one torque sensor configured to measure a torque exerted by the actuator assembly,
   wherein movement of the actuator causes a corresponding relative rotation between the proximal connection member and the tibial member, and
   wherein there is only one powered actuator between the proximal connection member and the tibial member.

2. The actuated prosthesis of claim 1, wherein the actuator assembly is provided at a rear portion of the prosthesis.

3. The actuated prosthesis of claim 1, wherein the proximal connection member comprises a socket connector.

4. The actuated prosthesis of claim 1, further comprising a controller to control the powered actuator, the controller outputting control signals in response to input signals from at least the torque sensor.

5. The actuated prosthesis of claim 4, wherein the controller has an output connected to a power drive, the power drive supplying electrical energy to the powered actuator, coming from a power source, in response to the control signals.

6. The actuated prosthesis of claim 4, wherein the input signals further comprise signals from sensors mounted on the prosthesis and located outside the prosthesis.

7. The actuated prosthesis of claim 1, wherein the tibial member comprises a bottom portion configured to operatively connect to a foot prosthesis.

8. The actuated prosthesis of claim 1, wherein the powered actuator is a linear actuator.

9. The actuated prosthesis of claim 1, wherein the proximal connection member and the tibial member are directly rotatably connected.

10. The actuated prosthesis of claim 1, wherein the proximal connection member and the tibial member are indirectly rotatably connected by the actuator assembly.

11. The actuated prosthesis of claim 1, wherein the proximal connection member and the tibial member are both directly rotatably connected, and indirectly rotatably connected by the actuator assembly.

12. The actuated prosthesis of claim 1, wherein the powered actuator is a motor.

13. The actuated prosthesis of claim 12, wherein the motor is a rotary motor.

14. The actuated prosthesis of claim 12, wherein the motor can provide power in two directions.

15. The actuated prosthesis of claim 1, wherein the torque sensor measures compression of the elastic member while the actuator is actuated.

16. The actuated prosthesis of claim 1, wherein the actuator assembly is configured to provide relatively stable force control.

17. The actuated prosthesis of claim 1, wherein the prosthesis comprises only one actuator assembly.

18. The actuated prosthesis of claim 1, wherein the elastic member allows for shock absorption while the actuator is actuated.

19. The actuated prosthesis of claim 1, wherein the elastic member allows for energy storage while the actuator is actuated.

20. An actuated prosthesis, the prosthesis comprising:
 a connector configured to operatively connect the actuated prosthesis to an amputee;
 a first member operatively connected to the connector;
 an actuator assembly comprising a first end, a second end, a powered actuator, and a mechanical elastic member spaced from the powered actuator, the powered actuator and the mechanical elastic member being positioned in series between the first and second ends, the actuator assembly being operatively connected to the first member at the first end, the mechanical elastic member configured to store energy during use of the actuated prosthesis independent of rotary movement of the powered actuator;
 a second member operatively connected to the second end of the actuator assembly and rotatably connected to the first member at least by the actuator assembly and a first pivot assembly such that the first member and the second member rotate relative to each other about a first pivot axis, the second member also rotatably connected to the first member by a second pivot assembly independent of the actuator assembly;
 at least one torque sensor configured to measure a torque exerted by the actuator assembly; and
 a controller configured to control the powered actuator based at least in part on signals from the at least one torque sensor;
 wherein rotary movement of the powered actuator causes a corresponding relative rotation between the first member and the second member about a second pivot axis associated with the second pivot assembly, and the relative rotation is affected at least in part by the controller by way of the powered actuator, and
 wherein the relative rotation is affected by only one powered actuator.

21. The actuated prosthesis of claim 20, wherein the actuator assembly is provided at a rear portion of the prosthesis.

22. The prosthesis according to claim 20, wherein the controller has an output connected to a power drive, the power drive supplying electrical energy to the powered actuator, coming from a power source, in response to the signals from the at least one torque sensor.

23. The prosthesis according to claim 22, wherein the power drive is also configured to supply electrical energy to the powered actuator in response to signals from sensors mounted on the prosthesis and located outside the prosthesis.

24. The actuated prosthesis of claim 20, wherein the powered actuator is a linear actuator.

25. The actuated prosthesis of claim 20, wherein the actuated prosthesis is a knee joint prosthesis.

26. The actuated prosthesis of claim 20, wherein the second member is a tibial member.

27. The actuated prosthesis of claim 20, wherein the first and second members are directly rotatably connected by the second pivot assembly.

28. The actuated prosthesis of claim 20, wherein the first and second members are indirectly rotatably connected by the actuator assembly.

29. The actuated prosthesis of claim 20, wherein the first and second members are both directly rotatably connected by the second pivot assembly, and indirectly rotatably connected by the actuator assembly.

30. The actuated prosthesis of claim 20, wherein the powered actuator is a motor.

31. The actuated prosthesis of claim 30, wherein the motor is a rotary motor.

32. The actuated prosthesis of claim 30, wherein the motor can provide power in two directions.

33. The actuated prosthesis of claim 20, wherein the at least one torque sensor measures torque by measuring compression of the elastic member while the actuator is actuated.

34. The actuated prosthesis of claim 20, wherein the actuator assembly is configured to provide relatively stable force control.

35. The actuated prosthesis of claim 20, wherein the prosthesis comprises only one actuator assembly between the first member and the second member.

36. The actuated prosthesis of claim 20, wherein the elastic member allows for shock absorption while the actuator is actuated.

37. The actuated prosthesis of claim 20, wherein the elastic member allows for energy storage while the actuator is actuated.

38. An actuated prosthesis to replace the knee joint of an amputee, the prosthesis comprising:
 a proximal male pyramid connector;
 a first prosthetic member connected to the proximal male pyramid connector;
 a second prosthetic member pivotally connected to the first prosthetic member to provide relative rotation between the first and second prosthetic members;
 an actuator assembly comprising a motor primarily powered by electricity, and an elastic member in series with and spaced from the motor, the actuator assembly configured to affect the relative rotation between the first and second prosthetic members at a position corresponding to a natural knee joint, the elastic member and the powered actuator being positioned distally from the knee joint; and
 a controller configured to control the actuator assembly in response to input signals from one or more sensors, at least one of said one or more sensors configured to measure compression of the elastic member while the actuator is actuated, wherein the at least one sensor configured to measure compression of the elastic member is configured to provide an estimate of torque on the prosthesis while the actuator is actuated.

39. The actuated prosthesis of claim 38, wherein the first prosthetic member comprises a knee member and the second prosthetic member comprises a trans-tibial member.

40. The actuated prosthesis of claim 38, wherein the first prosthetic member and the second prosthetic member form part of a leg prosthesis.

41. The actuated prosthesis of claim 40, wherein the leg prosthesis comprises an artificial foot.

42. The actuated prosthesis of claim 38, wherein there is only one motor that affects relative rotation between the first and second prosthetic members.

43. The actuated prosthesis of claim 38, wherein the elastic member is configured to provide shock absorption.

44. The actuated prosthesis of claim 38, wherein the elastic member is configured to provide energy storage.

45. The actuated prosthesis of claim 38, wherein the motor can provide power in two directions.

46. The actuated prosthesis of claim 38, wherein the actuator assembly is configured to provide relatively stable force control.

47. The actuated prosthesis of claim 38, further comprising a socket connected to the proximal male pyramid connector.

* * * * *